US010695264B2

(12) United States Patent
Taylor et al.

(10) Patent No.: US 10,695,264 B2
(45) Date of Patent: Jun. 30, 2020

(54) CPR CHEST COMPRESSION SYSTEM WITH RATE-BASED PATIENT TRANQUILITY MODE

(71) Applicant: Jolife AB, Lund (SE)

(72) Inventors: Tyson G. Taylor, Bothell, WA (US); Alex Esibov, Seattle, WA (US); Bjarne Madsen Hardig, Lund (SE); Fred Chapman, Newcastle, WA (US); Robert G. Walker, Seattle, WA (US); Gregory T. Kavounas, Bellevue, WA (US)

(73) Assignee: JOLIFE AB, Lund (SE)

( * ) Notice: Subject to any disclaimer, the term of this patent is extended or adjusted under 35 U.S.C. 154(b) by 912 days.

(21) Appl. No.: 15/298,045

(22) Filed: Oct. 19, 2016

(65) Prior Publication Data
US 2017/0035650 A1    Feb. 9, 2017

Related U.S. Application Data

(63) Continuation-in-part of application No. 14/642,027, filed on Mar. 9, 2015, now Pat. No. 10,117,804, and
(Continued)

(51) Int. Cl.
*A61H 31/00* (2006.01)
*G09B 5/06* (2006.01)
(Continued)

(52) U.S. Cl.
CPC ............. *A61H 31/005* (2013.01); *A61B 5/02* (2013.01); *A61B 5/04* (2013.01); *A61B 5/1032* (2013.01);
(Continued)

(58) Field of Classification Search
CPC .... A61H 31/00; A61H 31/004; A61H 31/005; A61H 2230/04; A61N 1/39
See application file for complete search history.

(56) References Cited

U.S. PATENT DOCUMENTS

| 4,326,507 A | 4/1982 | Barkalow |
| 6,939,315 B2 | 9/2005 | Sherman et al. |

(Continued)

OTHER PUBLICATIONS

Callahan, Thomas, Letter regarding approval of marketing Thumper® Model 1007, 1997, pp. 6-7 of 307 & pp. 194-195/307, Food and Drug Administration, Rockville, MD.
(Continued)

*Primary Examiner* — Justine R Yu
*Assistant Examiner* — Christopher E Miller
(74) *Attorney, Agent, or Firm* — Miller Nash Graham and Dunn

(57) ABSTRACT

A CPR system includes a retention structure to retain the patient's body, and a compression mechanism to perform CPR compressions to the patient's chest. The CPR system further includes a processor to control the compression mechanism, and thus the performance of the CPR compressions. In embodiments, the CPR system compresses at a rate or frequency that is purposely sub-optimal for circulation at least some of the time, and especially when it is detected that the patient has regained consciousness. An advantage can be that the patient may thus faint again, and therefore perceive less of the unpleasant experience of the mechanical chest compressions that the CPR system continues to perform on them as it preserves them alive.

31 Claims, 19 Drawing Sheets

Related U.S. Application Data a continuation-in-part of application No. 14/273,593, filed on May 9, 2014, now abandoned, and a continuation-in-part of application No. 14/271,660, filed on May 7, 2014, now Pat. No. 10,143,619.

(60) Provisional application No. 62/243,620, filed on Oct. 19, 2015, provisional application No. 62/243,617, filed on Oct. 19, 2015, provisional application No. 62/243,613, filed on Oct. 19, 2015.

(51) Int. Cl.

| | | |
|---|---|---|
| G09B 23/28 | (2006.01) | |
| A61B 5/02 | (2006.01) | |
| A61B 5/00 | (2006.01) | |
| A61B 5/103 | (2006.01) | |
| A61B 5/113 | (2006.01) | |
| A61B 5/04 | (2006.01) | |
| G16H 20/30 | (2018.01) | |
| G16H 20/40 | (2018.01) | |
| A61H 9/00 | (2006.01) | |
| A61B 7/00 | (2006.01) | |

(52) U.S. Cl.
CPC ............ *A61B 5/113* (2013.01); *A61B 5/4836* (2013.01); *A61B 5/747* (2013.01); *A61H 31/006* (2013.01); *G09B 5/06* (2013.01); *G09B 23/288* (2013.01); *G16H 20/30* (2018.01); *G16H 20/40* (2018.01); *A61B 7/00* (2013.01); *A61B 2505/01* (2013.01); *A61H 9/0057* (2013.01); *A61H 2201/0176* (2013.01); *A61H 2201/0184* (2013.01); *A61H 2201/0188* (2013.01); *A61H 2201/1207* (2013.01); *A61H 2201/1246* (2013.01); *A61H 2201/1463* (2013.01); *A61H 2201/5005* (2013.01); *A61H 2201/5007* (2013.01); *A61H 2201/5012* (2013.01); *A61H 2201/5035* (2013.01); *A61H 2201/5043* (2013.01); *A61H 2201/5046* (2013.01); *A61H 2201/5048* (2013.01); *A61H 2201/5058* (2013.01); *A61H 2201/5069* (2013.01); *A61H 2201/5079* (2013.01); *A61H 2201/5084* (2013.01); *A61H 2201/5092* (2013.01); *A61H 2201/5094* (2013.01); *A61H 2201/5097* (2013.01); *A61H 2230/045* (2013.01); *A61H 2230/065* (2013.01); *A61H 2230/105* (2013.01); *A61H 2230/206* (2013.01); *A61H 2230/208* (2013.01); *A61H 2230/25* (2013.01); *A61H 2230/255* (2013.01); *A61H 2230/305* (2013.01)

(56) References Cited

U.S. PATENT DOCUMENTS

| | | | |
|---|---|---|---|
| 7,410,470 B2* | 8/2008 | Escudero | A61H 31/005 601/41 |
| 7,569,021 B2 | 8/2009 | Sebelius et al. | |
| 2004/0015191 A1* | 1/2004 | Otman | A61N 1/37282 607/5 |
| 2004/0039313 A1* | 2/2004 | Sherman | A61H 31/00 601/21 |
| 2004/0230140 A1* | 11/2004 | Steen | A61H 31/008 601/41 |
| 2006/0094991 A1* | 5/2006 | Walker | A61H 31/004 601/41 |
| 2006/0173500 A1* | 8/2006 | Walker | A61B 5/046 607/5 |
| 2007/0225623 A1* | 9/2007 | Freeman | A61N 1/39 601/41 |
| 2010/0326442 A1* | 12/2010 | Hamilton | A61H 9/0078 128/204.21 |
| 2011/0092864 A1* | 4/2011 | Woerlee | A61H 31/00 601/41 |
| 2012/0016279 A1* | 1/2012 | Banville | A61H 31/004 601/41 |
| 2012/0330199 A1* | 12/2012 | Lurie | A61H 9/0078 601/41 |
| 2013/0296727 A1* | 11/2013 | Sullivan | A61B 5/046 600/513 |
| 2014/0342330 A1* | 11/2014 | Freeman | G09B 23/288 434/265 |
| 2015/0005588 A1* | 1/2015 | Herken | A61B 7/04 600/301 |
| 2015/0051521 A1* | 2/2015 | Woerlee | A61H 31/005 601/41 |
| 2015/0088016 A1* | 3/2015 | Fleischacker | A61N 1/3925 600/510 |
| 2015/0164339 A1* | 6/2015 | Xu | A61B 5/024 600/324 |
| 2015/0265497 A1* | 9/2015 | Kaufman | A61H 31/005 601/41 |
| 2016/0143804 A1* | 5/2016 | Nilsson | A61H 31/005 601/41 |
| 2016/0270673 A1* | 9/2016 | Aelen | A61B 7/00 |
| 2016/0296167 A1* | 10/2016 | Kantor | A61M 16/0051 |
| 2016/0317385 A1* | 11/2016 | Salcido | A61H 31/005 |
| 2016/0339198 A1* | 11/2016 | Fraser | A61M 11/02 |
| 2016/0374623 A1* | 12/2016 | Wijshoff | A61B 5/14551 600/301 |

OTHER PUBLICATIONS

A. Olaussen, M. Shepherd, Z. Nehme, K. Smith, S. Bernard, B. Mitra, Return of consciousness during ongoing cardiopulmonary resuscitation: A systematic review, Review article, Resuscitation 86, 2015, pp. 44-48, Elsevier.

A. Olaussen, M. Shepherd, Z. Nehme, K. Smith, Paul A. Jennings S. Bernard, B. Mitra, CPR-induced consciousness: A cross-sectional study of health care practitioners' experience, Australasian Emergency Nursing Journal 19, 2016, pp. 186-190, Elsevier.

Physio-Control, Inc., LUCAS® Chest Compression System, Product Brochure, May 2012.

Babbs, C. F., Efficacy of interposed abdominal compression-cardiopulmonary resuscitation (CPR), active compression and decompression-CPR, and Lifestick CPR: Basic physiology in a spreadsheet model, Crit. Care Med 2000 vol. 28, No. 11 (Suppl.), pp. N199-N202.

Cha, Kyoung Chul; Kim, Yeong Jun; Shin, Hyung Jin; Cha, Yong Sung; Kim, Hyun; Lee, Kang Hyun; Kwon, Woocheol; Hwang, Sung Oh, Optimal position for external chest compression during cardiopulmonary resuscitation: an analysis based on chest CT in patients resuscitated from cardiac arrest, Emerg Med J (2012). doi:10.1136/emermed-2012-201556; EMJ Online Jul. 25, 2012, Produced by BMJ Publishing Group Ltd under licence, pp. 1-5.

Eric Qvigstad, Jo Kramer-Johansen, Øystein Tømte, Tore Skålhegg, Øyvar Sørensen, Kjetil Sunde, Theresa M. Olasveengen, Clinical pilot study of different hand positions during manual chest compressions monitored with capnography, Resuscitation 84 (2013) 1203-1207, Clinical paper, Elsevier Ireland Ltd.

\* cited by examiner

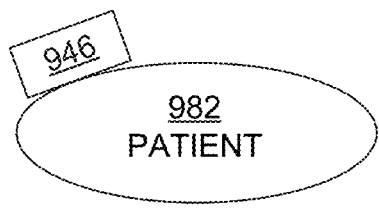
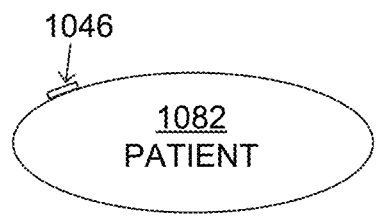
FIG. 9     FIG. 10
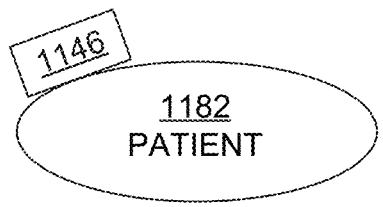
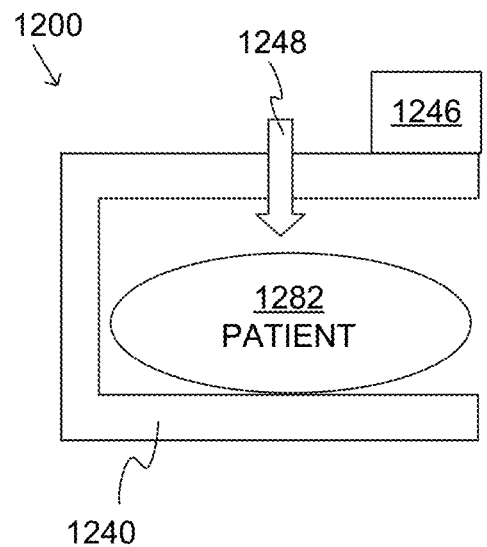
FIG. 11     FIG. 12

FIG. 26   METHODS

CPR CHEST COMPRESSION SYSTEM WITH RATE-BASED PATIENT TRANQUILITY MODE

CROSS REFERENCE TO RELATED PATENT APPLICATIONS

This patent application claims priority from U.S. Provisional Patent Application Ser. No. 62/243,613, filed on Oct. 19, 2015, and also from U.S. Provisional Patent Application Ser. No. 62/243,617, filed on Oct. 19, 2015, and also from U.S. Provisional Patent Application Ser. No. 62/243,620, filed on Oct. 19, 2015, and is a Continuation-In-Part of co-pending U.S. patent application Ser. No. 14/642,027, filed on Mar. 9, 2015, and is also a Continuation-In-Part of co-pending U.S. patent application Ser. No. 14/273,593, filed on May 9, 2014, and is also a Continuation-In-Part of co-pending U.S. patent application Ser. No. 14/271,660, filed on May 7, 2014, the disclosures of all of which, as initially made, are hereby incorporated by reference.

BACKGROUND

In certain types of medical emergencies a patient's heart stops working, which stops the blood from flowing. Without the blood flowing, organs like the brain will start becoming damaged, and the patient will soon die. Cardiopulmonary resuscitation (CPR) can forestall these risks. CPR includes performing repeated chest compressions to the chest of the patient, so as to cause the patient's blood to circulate some. CPR also includes delivering rescue breaths to the patient, so as to create air circulation in the lungs. CPR is intended to merely forestall organ damage and death, until a more definitive treatment is made available. Defibrillation is one such definitive treatment: it is an electric shock delivered deliberately to the patient's heart, in the hope of restoring the heart rhythm.

Traditionally, CPR has been performed manually. A number of people have been trained in CPR, including some who are not in the medical professions, just in case they are bystanders in a medical emergency event.

Manual CPR may be ineffective, however. Indeed, the rescuer might not be able to recall their training, especially under the stress of the moment. And even the best trained rescuer can become fatigued from performing chest compressions for a long time, at which point their performance may become degraded. In the end, chest compressions that are not frequent enough, not deep enough, or not followed by a full release may fail to maintain the blood circulation required to forestall organ damage and death.

The risk of ineffective chest compressions has been addressed with CPR chest compression machines. Such machines have been known by a number of names, for example CPR chest compression machines, CPR machines, mechanical CPR devices, cardiac compressors, CPR devices, CPR systems, and so on.

CPR chest compression machines typically hold the patient supine, which means lying on his or her back. Such machines then repeatedly compress and release the chest of the patient. In fact, they can be programmed to automatically follow the guidelines, by compressing and releasing at the recommended rate or frequency, while reaching a specific depth.

Guidelines by medical experts such as the American Heart Association provide parameters for CPR to cause the blood to circulate effectively. The parameters are for aspects such as the frequency of the chest compressions, the depth that they should reach, and the full release that is to follow each of them. If the patient is an adult, the depth is sometimes required to reach 5 cm (2 in.). The parameters for CPR may also include instructions for the rescue breaths.

International guidelines for performing cardiopulmonary resuscitation (CPR) recommend chest compressions that are consistent and repetitive in duty cycle, depth, and rate, among other characteristics. Furthermore, recommendations for hand placement during CPR are not more specific than pushing in the center of the chest at the sternum. This is, presumably, to press on the heart, or "pump," that generates blood flow.

The repeated chest compressions of CPR are actually compressions alternating with releases. The compressions cause the chest to be compressed from its original shape. During the releases the chest is decompressing, which means that the chest is undergoing the process of returning to its original shape. This decompressing does not happen immediately upon a quick release. In fact, full decompression might not be attained by the time the next compression is performed. In addition, the chest may start collapsing due to the repeated compressions, which means that it might not fully return to its original height, even if it were given ample opportunity to do so.

Some CPR chest compression machines compress the chest by a piston. Some may even have a suction cup at the end of the piston, with which these machines lift the chest at least during the releases. This lifting may actively assist the chest, in decompressing the chest faster than the chest would accomplish by itself. This type of lifting is sometimes called active decompression.

BRIEF SUMMARY

The present description gives instances of Cardio-Pulmonary Resuscitation (CPR), systems, storage media that store programs, and methods, the use of which may help overcome problems and limitations of the prior art.

In rate-based embodiments, a CPR system includes a retention structure to retain the patient's body, and a compression mechanism to perform CPR compressions to the patient's chest. The CPR system further includes a processor to control the compression mechanism, and thus the performance of the CPR compressions. In embodiments, the CPR system compresses at a rate or frequency that is purposely sub-optimal for circulation at least some of the time, and especially when it is detected that the patient has regained consciousness. An advantage can be that the patient may thus lose consciousness again by fainting, and therefore perceive less of the unpleasant experience of the mechanical chest compressions that the CPR system continues to perform on them as it preserves them alive.

The present description further gives instances of additional Cardio-Pulmonary Resuscitation (CPR), systems, storage media that store programs, and methods, the use of which may help overcome problems and limitations of the prior art.

In depth-based embodiments, a CPR system includes a retention structure to retain the patient's body, and a compression mechanism to perform CPR compressions to the patient's chest. The CPR system further includes a processor to control the compression mechanism, and thus the performance of the CPR compressions. In embodiments, the CPR system compresses at a depth that is purposely sub-optimal for circulation at least some of the time, and especially when it is detected that the patient has regained consciousness. An advantage can be that the patient may thus lose consciousness again by fainting, and therefore perceive less of the unpleasant experience of the mechanical chest compressions that the CPR system continues to perform on them as it preserves them alive.

The present description further gives instances of further Cardio-Pulmonary Resuscitation (CPR), systems, storage media that store programs, and methods, the use of which may help overcome problems and limitations of the prior art.

In embodiments, CPR systems include multiple compression mechanisms. Such a CPR system may include a retention structure to retain the patient's body, a main compression mechanism to perform main compressions to the patient's chest, and an auxiliary compression mechanism to perform auxiliary compressions to the body. The auxiliary compressions can be CPR compressions to the chest in coordination with the main compressions, or compressions to another part of the body such as the abdomen, optionally further with time variations. An advantage over the prior art is that synergistic effects may be accomplished, as the heart itself is not working at the time.

These and other features and advantages of the claimed invention will become more readily apparent in view of the embodiments described and illustrated in the present disclosure, namely from the present written specification and the drawings.

BRIEF DESCRIPTION OF THE DRAWINGS

FIG. 9 is a diagram of a patient with a sample consciousness detector that includes a motion detector according to embodiments.

FIG. 10 is a diagram of a patient with a sample consciousness detector that includes an electrode according to embodiments.

FIG. 11 is a diagram of a patient with a sample consciousness detector that includes a close-up camera according to embodiments.

FIG. 12 is a diagram of a CPR system with a sample consciousness detector that includes a camera according to embodiments.

DETAILED DESCRIPTION

Figure 1:
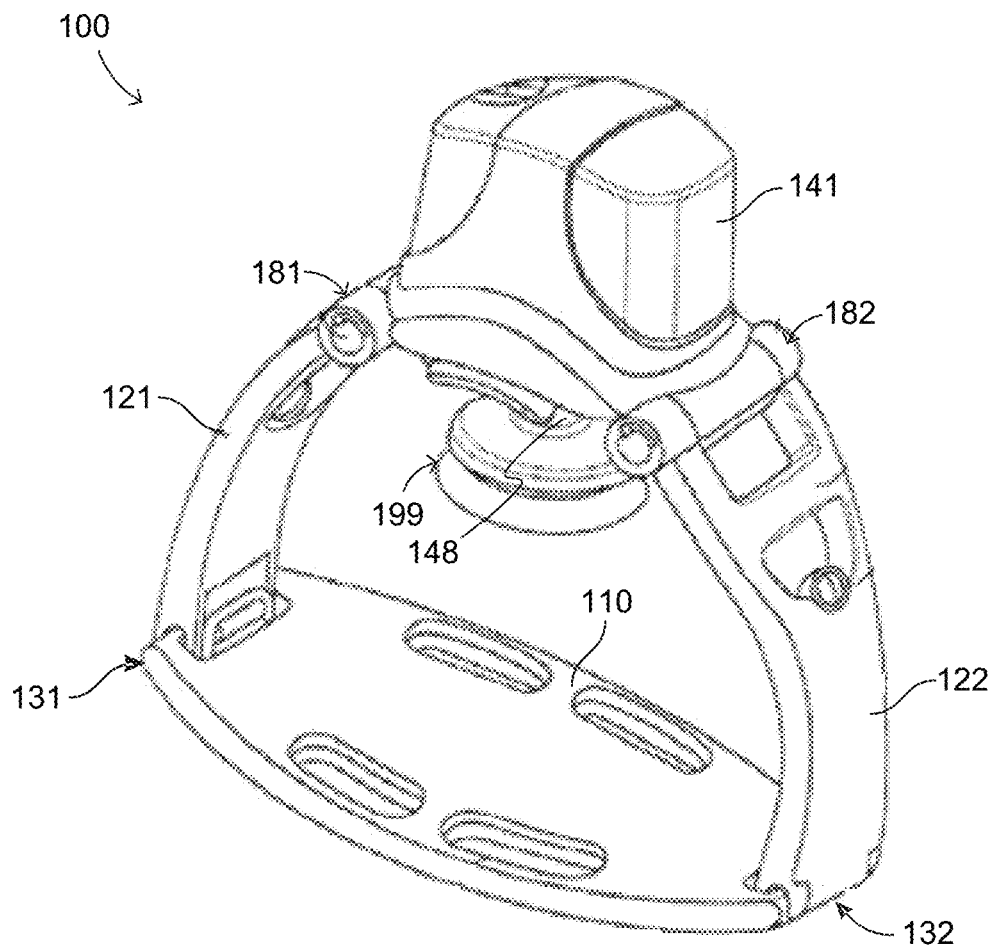
FIG. 1 is a perspective diagram of a conventional CPR system.

As has been mentioned, the present description is about Cardio-Pulmonary Resuscitation (CPR) systems that are usable by a rescuer to care for a patient. A conventional such system is now described with reference to FIG. 1, which is presently being sold by Physio-Control, Inc. under the trademark Lucas®.

A CPR system 100 includes components that form a retention structure. The components include a central member 141, a first leg 121, a second leg 122 and a back plate 110. Central member 141 is coupled with first leg 121 and second leg 122 using joints 181, 182, such that first leg 121 and second leg 122 can be partly rotated around joints 181, 182 with respect to central member 141. This rotation can help minimize the overall volume of CPR system 100, for easier storage at times when it is not used. In addition, the far ends of legs 121, 122 can become coupled with edges 131, 132 of back plate 110.

These couplings form the retention structure that retains the patient. In this particular case, central member 141, first leg 121, second leg 122 and back plate 110 form a closed loop, in which the patient is retained. For storage, back plate 110 can be uncoupled from legs 121, 121, which can be further rotated so that their edges are brought closer to each other.

Central member 141 includes a battery that stores energy, a motor that receives the energy from the battery, and a compression mechanism that can be driven by the motor. The compression mechanism is driven up and down by the motor using a rack and pinion gear. The compression mechanism includes a piston 148 that can compress and release the patient's chest. Here, piston 148 terminates in a suction cup 199 for active decompression. In this case the battery, the motor and the rack and pinion gear are not shown, because they are completely within a housing of central member 141.

Physio-Control's Lucas® system has performed so well in restoring blood circulation to the patient that, during the system's operation, sometimes the patient actually wakes up. The reason is that, even though the patient's heart is not beating by itself, the CPR system is effectively performing the heart's function for the patient and restores their circulation. This is a significant milestone in the achieved effectiveness of CPR systems, and definitely an argument for using CPR machines over manual CPR. A challenge, however, is that the now awake patient experiences the compressions, which tends to be unpleasant. So far, this problem has been addressed by sedating the patient.

Figure 2:
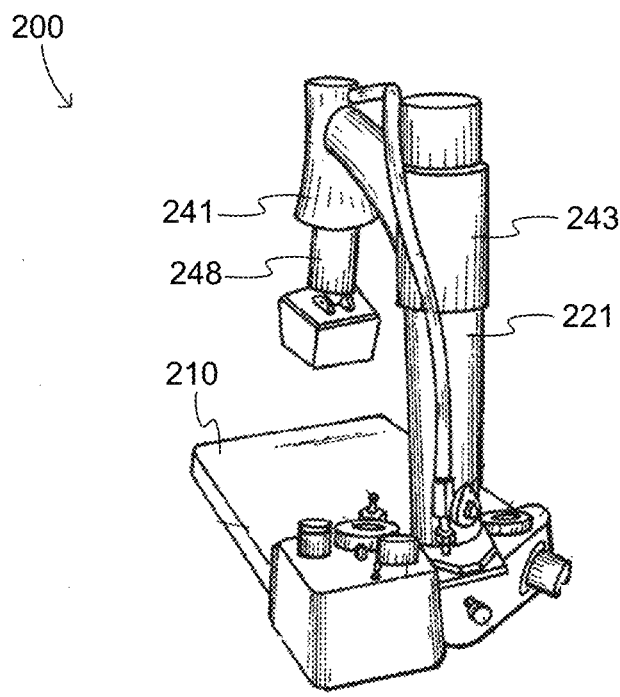
FIG. 2 shows elements of a diagram in a prior art reference for a CPR system.

FIG. 2 shows elements of a diagram of prior U.S. Pat. No. 4,326,507, and in particular FIG. 2 of the present document repeats selected features of that prior patent's FIG. 1. Specifically, in the present document, FIG. 2 shows another CPR system 200 having a platform 210, on which the patient (not shown) may be placed on their back. A vertical removable upstanding column or support 221 is attached to the edge of platform 210, thus rising next to the patient. A releasable collar 243 supports an overhanging beam or arm 241 over platform 210. A plunger piston 248 emerges from overhanging beam or arm 241, for compressing downwards the chest of the patient who is supine on platform 210.

Figure 3:
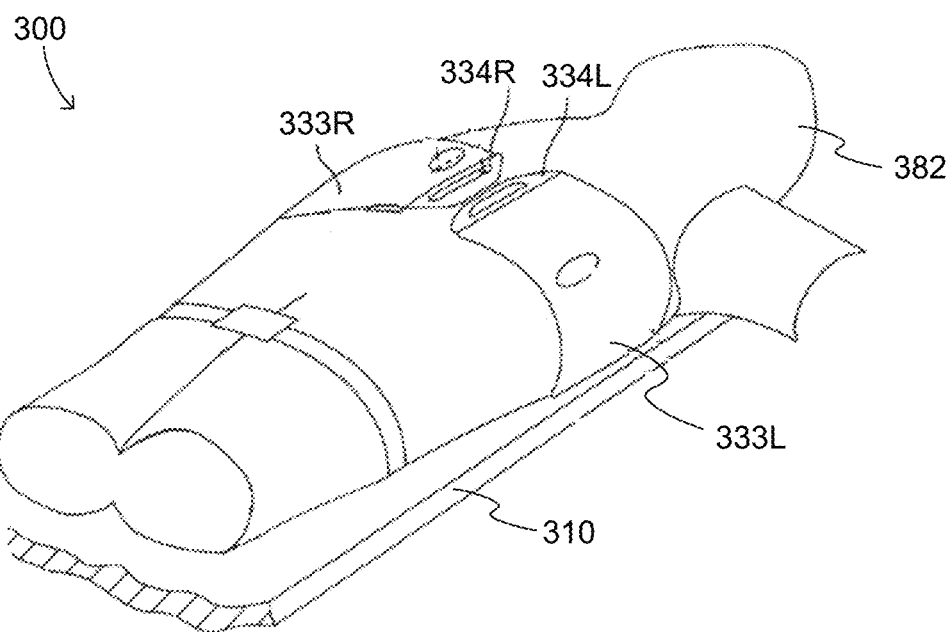
FIG. 3 shows elements of a diagram in another prior art reference for a CPR system.

FIG. 3 shows elements of a diagram of prior U.S. Pat. No. 6,939,315, and in particular FIG. 3 of the present document repeats selected features of that prior patent's FIG. 6. Specifically, in the present document, FIG. 3 shows another CPR system 300 having a platform 310, on which a patient 382 may be placed supine. A left side 333L of a chest compression belt terminates in a left buckle 334L, and a right side 333R of the chest compression belt terminates in a right buckle 334R. The chest compression belt can be buckled by joining left buckle 334L together with right buckle 334R. Then a motor (not shown in this FIG.) retracts and releases the buckled belt, so as to constrict and relax the chest of patient 382.

Embodiments are now described in more detail.

Figure 4:
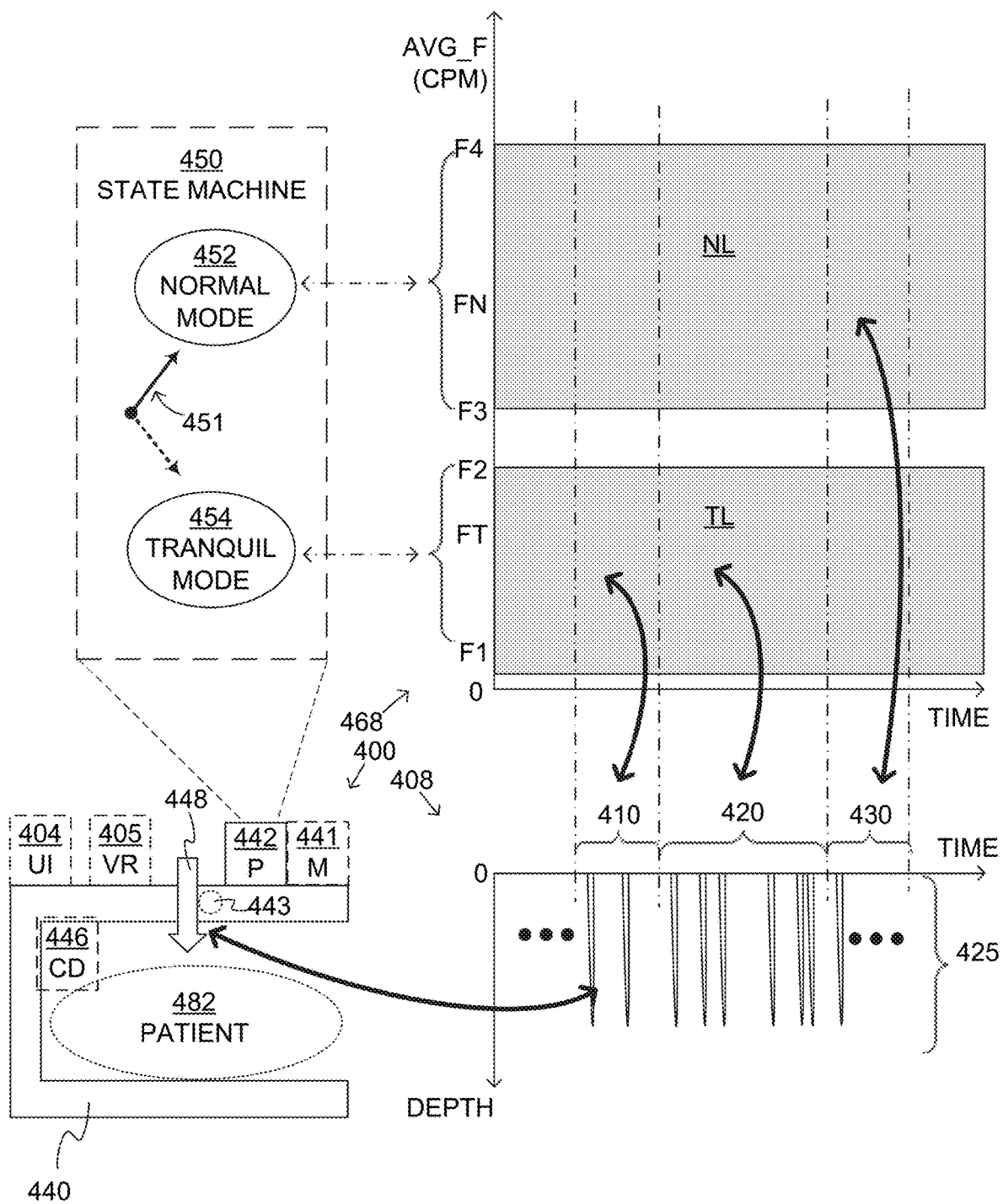
FIG. 4 is a diagram showing an aspect of a sample conceptual CPR system made according to frequency-based embodiments, in combination with cooperating aspects illustrating operations of the CPR system according to related embodiments.

FIG. 4 is a diagram of an aspect of a conceptual Cardio-Pulmonary Resuscitation (CPR) system 400, in combination with cooperating aspects 408, 468 illustrating operations according to embodiments of CPR system 400. It will be appreciated that, while CPR system 400 is general, cooperating aspects 408, 468 illustrate operations according to embodiments that are rate-based.

CPR system 400 is usable by a rescuer (not shown) to care for a patient 482. As will be appreciated, the rescuer will thus place patient 482 in CPR system 400, and turn on CPR system 400. Afterwards, CPR system 400 may operate automatically and largely autonomously, while the rescuer is observing, making adjustments, possibly sedating the patient if the latter regains consciousness, performing other tasks, or making logistical arrangements for transport and subsequent care of patient 482.

CPR system 400 includes a retention structure 440 that is configured to retain the body of patient 482. It will be appreciated that retention structure 440 is shown here conceptually, and not implemented by any particular configuration, as there can be many ways in which retention structure 440 may be implemented. For example, retention structure 440 may include a central member, a first leg, a second leg and a back plate. The central member can be configured to become coupled to the back plate via the first leg and the second leg. This could be as shown in FIG. 1, where the back plate can be totally separated from the other three components. Or, these components may be capable of being coupled together and separable in different combinations, for example using hinges or not, etc. Or a single leg may be used, for example as shown in FIG. 2 of this document where the patient is retained between platform 210 and plunger piston 248. Or a belt may be used to retain the patient from the chest onto a back board, back plate or platform, for example as shown in FIG. 3 of this document.

In some embodiments, straps (not shown) may be used to further secure the patient onto a back board, back plate or platform of retention structure 440. Such straps may prevent shifting of the patient's body with respect to retention structure 440 during the compressions, etc.

CPR system 400 also includes a compression mechanism 448 that is attached to retention structure 440. Again, it will be appreciated that compression mechanism 448 is shown here conceptually, and not implemented by any particular configuration, as there can be many ways in which compression mechanism 448 may be implemented. Of course, the implementation of compression mechanism 448 is preferably done in consideration of the implementation of retention structure 440.

In some embodiments, compression mechanism 448 is a piston that emerges from a housing that is placed against the patient's chest. In such embodiments, retention structure 440 can include a belt with two ends attached to the housing. In such versions, the belt is wrapped around the back of the patient to encircle the torso.

Compression mechanism 448 can be configured to perform, while the body of patient 482 is thus retained by retention structure 440, automatically CPR compressions alternating with releases to a chest of the body of patient 482. For example, compression mechanism 448 can be driven by a motor 443.

CPR system 400 may further include a processor (P) 442 coupled to retention structure 440. Of course, processor 442 may be embedded in a housing of retention structure 440, and so on. Processor 442 may be implemented by one or more digital logic devices, such as microprocessors, FPGAs, etc. Processor 442 may interoperate with an optional memory (M) 441, etc.

As will be described later in more detail, in some versions or embodiments of the invention, processor 442 is capable of operating in different modes. In the example of FIG. 4, at least a normal mode 452 and a tranquil mode 454 are possible. Tranquil mode 454 has been named from the fact that patient 482 will be less disturbed, and thus more tranquil, by receiving the chest compressions from the CPR system 400 that continues to keep them alive and preserve their organs from being damaged. Otherwise, a patient that is semi- or fully conscious could experience excessive pain and suffering, and even post-traumatic stress disorder. Operation in the tranquil mode may provide the opportunity for preparation and proper sedation of the patient, after which optimal blood flow can be constituted again.

In some versions, processor 442 includes a state machine 450, and is able to choose its mode of operation by a selector 451. In the example of FIG. 4, selector 451 has selected normal mode 452.

Processor 442 can be configured to control compression mechanism 448 to operate in certain ways according to embodiments. Of course, where motor 443 is used, processor 442 can be configured to control compression mechanism 448 by controlling the operation of motor 443.

Controlling compression mechanism 448 according to embodiments is now described in more detail. First, since the chest compressions are intended for CPR, the controlling can be such that the CPR compressions cause the chest to become compressed by at least 2 cm, at least for an adult. In fact, larger compression depths are advised by the American Heart Association (AHA), such as 5 cm (1"-2"), or even deeper. Such compression depths are achieved by CPR systems sold in the market in the year 2016.

Moreover, according to versions or embodiments of the invention, compression mechanism 448 can be further controlled so as to intentionally underperform, at least temporarily, from what it could do or at least from what is advised by the AHA Guidelines for optimum blood circulation. This underperforming can cause the patient to lose consciousness again by fainting, which can have the advantage that the patient will become more tranquil and experience less of the unpleasant experience of the mechanical chest compressions that the CPR system continues to perform on them.

Versions or embodiments of the invention can intentionally underperform in this manner in a number of ways. One such way is to reduce the frequency of the compressions, as is described later in more detail at least with reference to FIG. 28. Another is to reduce the depth of the compressions. Yet another is to alter the shape of the compression/release/ (decompression) waveform. One more is to affect the duty ratio of the compressions. One more is any combination of the above. In embodiments of variable chest compression CPR, different combinations of parameters may preferentially generate blood flow to a specific part of the body. For example, faster compressions may direct more blood to the brain while slower compressions may direct blood to the heart instead of the brain. In versions, compressions are optimized for the heart or lungs instead of the brain, thereby maintaining overall total blood flow at or near optimum, while still inducing unconsciousness by directing that flow towards organs other than the brain. These adjustments can be initiated directly, or after a short pause that will ensure that the patient will again lose consciousness.

In some versions, the frequency of the compressions is reduced. A convenient way of measuring the frequency in this art is in the units of compressions per minute (cpm). For example, since 15 sec is ¼ of a minute, the average frequency of compressions during a time interval that lasts 15 sec can be given by the number of compressions performed during that interval times 4.

Some particular values for the frequency of chest compressions by compression mechanism 448 are now described referring to aspect 408, which is a time diagram of compressions. In aspect 408, time is depicted in the horizontal axis while compression depth is depicted in the vertical axis, increasing in a downward direction. Some sample compressions 425 are shown for a first time interval 410, a second time interval 420 that immediately follows first time interval 410, and an other time interval 430 that is different from both intervals 410, 420. Compressions 425 are shown generically as to their shape, exact depth, and timing, in the sense that they could have any duty ratio and their individual downward waveforms could have any shape.

In some versions, first time interval 410 lasts 15 sec. During first time interval 410, the compressions can be performed at an average frequency between 0.5 cpm and 52 cpm. In fact, instead of 52 cpm, the maximum can be even lower, such as at most 48 cpm, 44 cpm, 40 cpm, or even lower.

Further, in some versions, second time interval 420 lasts 30 sec or longer. During second time interval 420, the average frequency is between 0.5 cpm and 52 cpm. The maximum could actually be higher, such as 56 cpm. Or, the maximum can be lower, such as at most 48 cpm, 44 cpm, 40 cpm, or even lower.

Moreover, in some versions, other time interval 430 lasts at least 15 sec, and often much longer. During other time interval 430, the CPR compressions can be performed at an average frequency of at least 64 cpm.

In FIG. 4, aspect 468 is a time diagram of average frequencies. In particular, for each moment on the time axis, an average frequency around that moment is computed and plotted for a value on the vertical AVG_F axis.

It will be appreciated how aspect 468 cooperates with aspect 408. Indeed, during the above described first time interval 410, the average frequency falls within a lower band TL, which is bounded by frequency values F1, F2. Sample values for F1, F2 were given above. Moreover, during the above described second time interval 420, the average frequency falls within the same lower band TL, or a lower band that has different values, etc. This lower band TL corresponds to CPR system 400 underperforming, as was described above. In addition, for times outside first time interval 410 and second time interval 420, the average frequency could be at different frequencies, for example at higher band NL that is bounded by frequency values F3 and F4. This can be true, for example, for time interval 430. This upper band NL would correspond to normal operation, F3 could be 60 cpm, and F4 much higher.

It will be further appreciated how aspect 468 also cooperates with state machine 450 of a yet different aspect in FIG. 4. Indeed, lower band TL corresponds to tranquil mode 454, while upper band NL corresponds to normal mode 452.

In aspect 468, suitable frequency values for lower band TL can be found by performance purposely deficient enough so that the patient does not regain consciousness, but also effective enough so that the patient's organs do not sustain damage. The upper frequency values mentioned above for F2, if they were those of the heart, are known to not be enough to maintain consciousness, at least to most people. It should be noted, however, that a person who has fainted is neither dead, nor necessarily dying.

Suitable frequency values for upper band NL can be found by performance that aims to improve circulation. For example, presently the AHA Guidelines recommend compressions at 100 cpm.

As all these possible frequency values are taken into effect, it will be understood that lower band TL may even overlap upper band NL. In other words, F2 could be larger than F3. Indeed, a very good frequency for the tranquil mode could be about 80 cpm. In the example of FIG. 4, the opposite case is shown only so as to facilitate the initial explanation. CPR system 400, however, can handle bands of different and even overlapping values. This way, CPR system 400 is advantageously better prepared for a range of patients who may have different resting heart rates to begin with, and for whom suitable values for upper band NL and lower band TL may be correspondingly different. In fact, as will be seen later, in embodiments a CPR system may search to find an optimal parameter for tranquil mode 454 for a specific patient, such as an optimal frequency.

It should be understood that, in aspect 408, sample compressions 425 are shown generically and not completely, so as to discuss how their total number as related to their average frequency, but not to indicate their actual distribution over time. More compressions could be included than what is shown, of the same or different depth, duty ratio, etc. Possible time distributions according to embodiments are now described for compressions 425, for example within first time interval 410 and second time interval 420.

Figure 5:
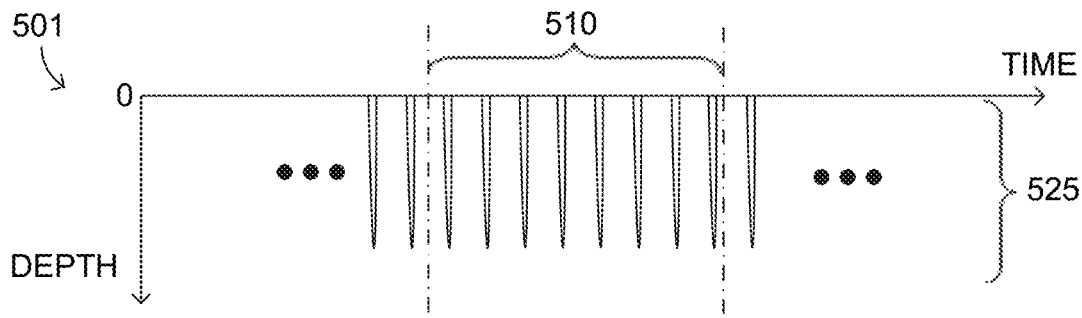
FIG. 5 is a time diagram showing a sample time distribution of chest compressions within a time interval according to an embodiment.

FIG. 5 is a time diagram 501. Diagram 501 shows a sample time distribution of chest compressions 525 within a time interval 510 according to an embodiment. Time interval 510 could be first time interval 410, second time interval 420, or both. In diagram 501, all compressions 525 during time interval 510 are performed at a single frequency. The time spacing between any two successive compressions is the same.

Figure 6:
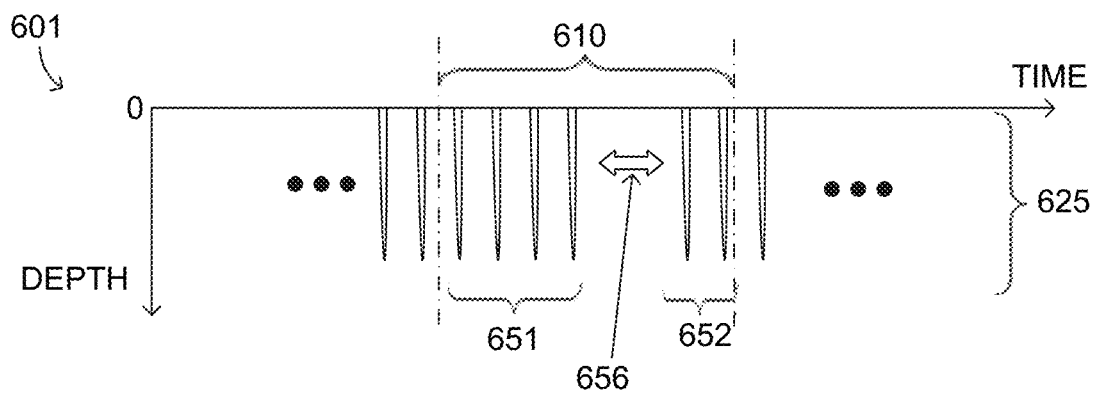
FIG. 6 is a time diagram showing a sample time distribution of chest compressions within a time interval according to another embodiment.

FIG. 6 is a time diagram 601. Diagram 601 shows a sample time distribution of chest compressions 625 within a time interval 610 according to another embodiment. Time interval 610 could be first time interval 410, second time interval 420, or both. In diagram 601, during time interval 610, compressions 625 are performed in two groups 651, 652 at a single frequency, while no compressions are performed during a set pause 656 between two groups 651, 652. Set pause 656 could last at least 3 sec, and separate different sets of chest compressions.

Figure 7:
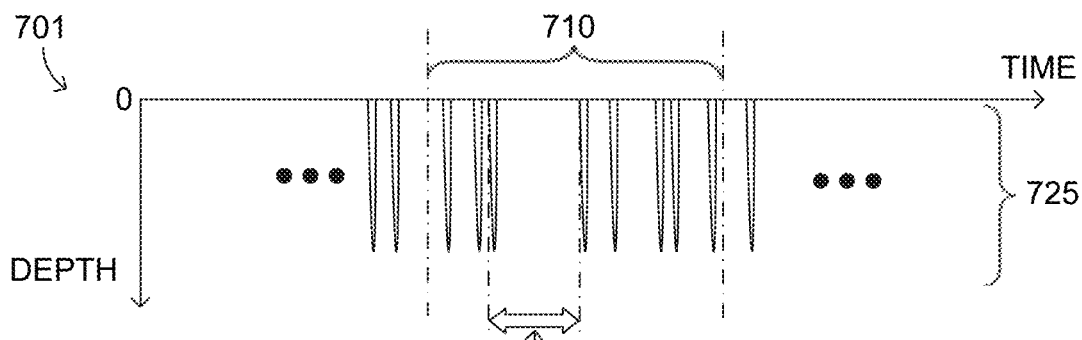
FIG. 7 is a time diagram showing a sample time distribution of chest compressions within a time interval according to one more embodiment.

FIG. 7 is a time diagram 701. Diagram 701 shows a sample time distribution of chest compressions 725 within a time interval 710 according to another embodiment. Time interval 710 could be first time interval 410, second time interval 420, or both. In diagram 701, during time interval 710, compressions 725 are performed at seemingly irregular times.

In such versions, at least some of compressions 725 are performed at a plurality of instantaneous frequencies. For purposes of this document, an instantaneous frequency INST_F is defined as a time spacing between two successive compressions. It is further preferred that the instantaneous frequency be defined from similar aspects of such successive compressions, if available. In the example of FIG. 7, such a time spacing 757 is shown, which is defined from the beginnings of two successive compressions.

Other embodiments are not rate-based, or not only rate-based. For example, some embodiments could achieve a tranquil mode in a mixed way, such as by being waveform-based. The waveform may be affected in different ways.

In some versions, the waveform could have different duty ratios. The duty ratio is a statistic for a ratio of how long the chest is being compressed by the downward portion of the waveform versus how long it takes to initiate successive compressions. As such, the duty ratio is always less than one. (If it were one, the compressions would not be distinct.)

Figure 27:
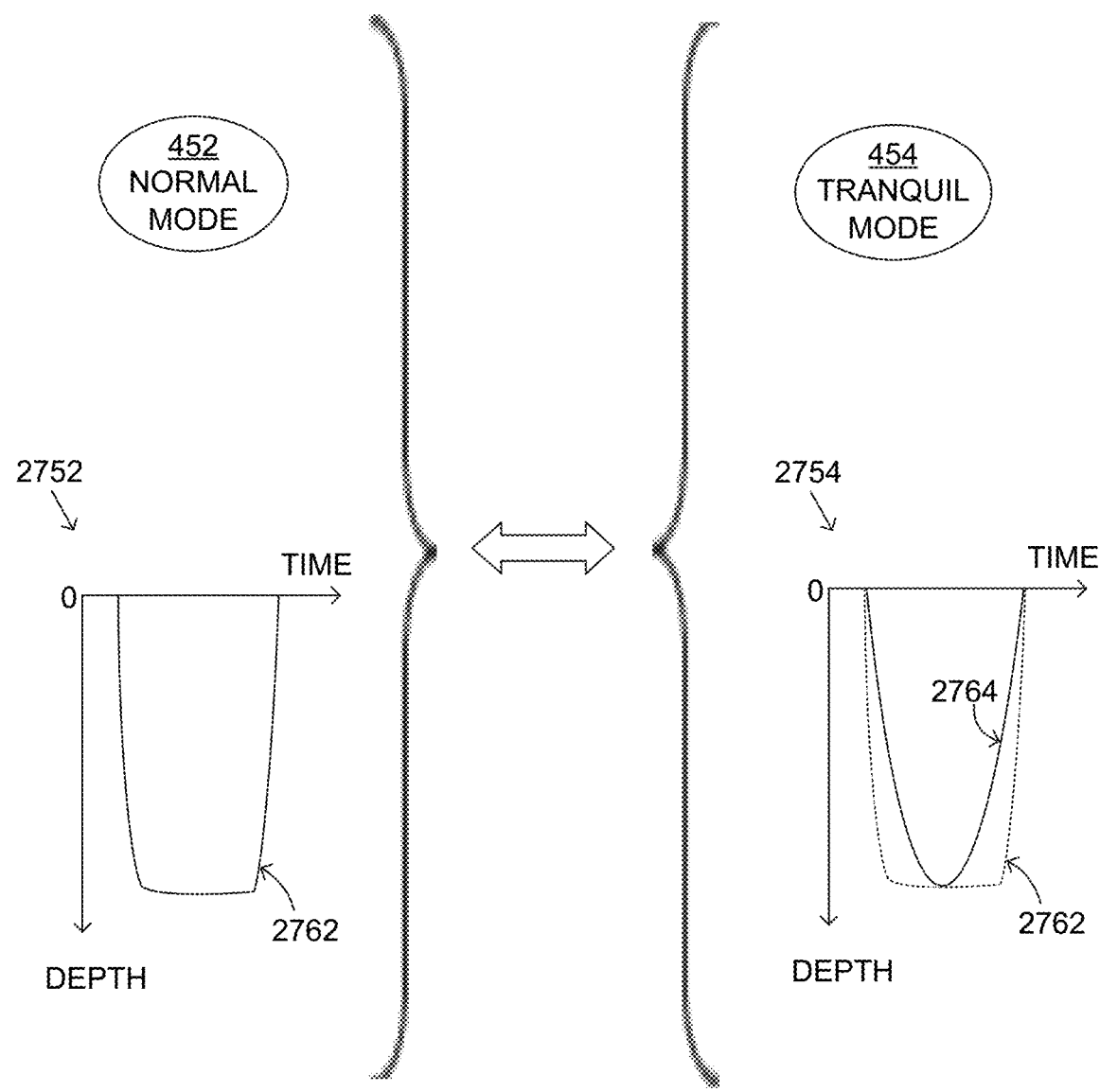
FIG. 27 is a diagram contrasting different compression and release waveforms for a waveform-based tranquil mode.

In some versions, it is the shape of the downward portion of the waveform, which is also known as the compression waveform. An example is seen in FIG. 27. For normal mode 452 a time diagram 2752 shows the compression-release waveform 2762, which is more trapezoidal-like. For tranquil mode 454 time diagram 2754 shows the compression-release waveform 2764. A compression with waveform 2764 might be less effective at moving blood, and also perhaps less uncomfortable, than a compression with waveform 2754. This example illustrates a number of possibilities:

For example, in versions the compression waveform could be such that it initially compresses less quickly in tranquil mode 454 than in normal mode 452. In other words, the initial downward stroke could have a first time derivative of a lesser absolute value in the tranquil mode than in the normal mode.

For another example, in versions, the compression waveform could be such that it has fewer sharper corners in tranquil mode 454 than in normal mode 452. In other words, the overall compression waveform could achieve one or more second time derivatives of a lesser absolute value in the tranquil mode than in the normal mode.

In some versions a consciousness detector is provided, and the CPR system's performance may change depending on outputs of the consciousness detector. Examples are now described.

Returning to FIG. 4, CPR system 400 may further include a consciousness detector (CD) 446. Consciousness detector 446 is shown conceptually in FIG. 4 and, at least from the description that follows, it will be recognized that different embodiments of consciousness detector 446 can have components placed at different locations, such as on the patient, at retention structure 440, etc.

Consciousness detector 446 can be configured to detect a patient parameter, and to output a series of consciousness values determined from the detected patient parameter. In fact, consciousness detector 446 can be configured to do this after at least 20 of the chest compressions have been performed.

Consciousness detector 446 can be further configured to be operatively coupled to processor 442. In such versions, then, processor 442 can be configured to receive the series of outputted consciousness values. An example is now described.

Figure 8:
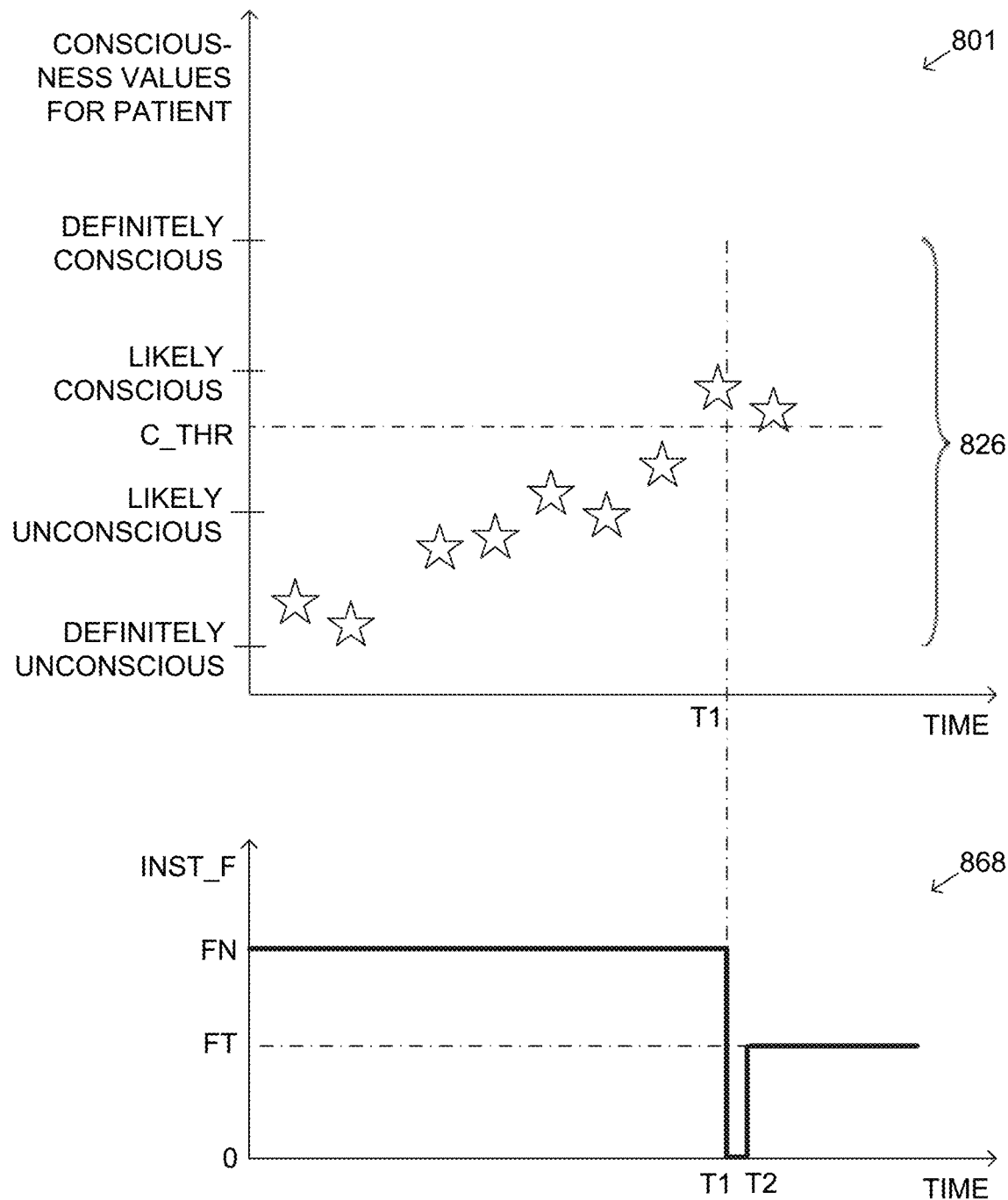
FIG. 8 shows a combination of a time diagram of a sample series of outputted consciousness values, along with a time diagram illustrating how an instantaneous frequency of the performed chest compressions can change in view of the outputted consciousness values according to embodiments.

FIG. 8 shows in combination a time diagram 801 and a time diagram 868, whose horizontal time axes are aligned. The time axis could start from the beginning of an event, at which time the patient is definitely unconscious, or at a different time.

In diagram 801, a series of consciousness values 826 are shown as stars at the times they are generated. These consciousness values 826 can have numerical values in a numerical scale that can initially have high resolution. A possible conversion to a coarser scale, one likely usable by processor 442 or by the attentive rescuer or both, is shown on the vertical axis of diagram 801, in terms of how the likely consciousness of the patient can be evaluated.

In addition, a threshold value C_THR could be postulated on the vertical axis, for this and/or other purposes. In this example, C_THR is postulated at the lower end of the "LIKELY CONSCIOUS" range of values.

In diagram 801 consciousness values 826 increase progressively as the CPR compressions are being performed over time, although this progress is not necessarily monotonic. The first consciousness values that crosses C_THR occurs at time T1. The subsequent one has a value that remains above C_THR.

In diagram 868, a time evolution is shown of an instantaneous frequency INST_F of the performed chest compressions. In this example, the instantaneous frequency INST_F starts and remains at a fixed value FN until time T1. Since the instantaneous frequency has remained constant then, until time T1, the average frequency has also remained constant at FN. In some versions, this frequency FN could correspond to a frequency within upper band NL of aspect 468 in FIG. 4. (In other examples, INST_F need not remain constant.)

In some versions, processor 440 can control compression mechanism 448 so as to change a current average frequency of performing the chest compressions from a first value FN to a second value FT. This can happen if, out of an early and a later consciousness value, in some instances the later consciousness value is different from the early consciousness value. In the example of FIG. 8, the later consciousness value occurs at time T1, while the early value can be any value prior to it. At time T1 the threshold value C_THR was crossed for the first time.

In diagram 868 then, at time T1, compressions stop entirely until a short time T2 thereafter, to ensure the patient will faint again. Then, at time T2, compressions resume at a second value FT, which is less than FN. In some versions, these frequencies FN, FT could correspond to frequencies within upper band NL and lower band TL of aspect 468 in FIG. 4. This frequency FT can be the current average frequency measured over a 15 sec interval.

The time between T1 and T2 is also known as a pause interval. It can be 15 sec or shorter. During the pause interval, INST_F=0. Of course, pausing the compressions during the pause interval is optional. The pause interval occurs after the later consciousness value is received at T1, and before T2, which is when the compressions start being performed at a current average frequency having the second value FT.

In the example of FIG. 8, the processor reacted at time T1, which is the first time any of the consciousness values 826 crossed C_THR. This need not be the case. In some instances, automatically transitioning to the lower value may have been disabled as a function, as described later in this document. Moreover, before triggering, it may be desirable to first accumulate a number of consciousness values in the series and ensure enough of them are above C_THR, for increased reliability.

As seen above, the CPR system's performance may change depending on outputs of the consciousness detector. In addition, or alternatively, a human-perceptible indication may be emitted from a user interface, if provided, as described later in this document.

Embodiments are now described for the consciousness detector.

FIG. 9 is a diagram of a patient 982 with a sample consciousness detector 946 that includes a motion detector. The motion detector can be configured to detect a motion of the patient. The motion can be a sign that the patient is waking up. Placing the motion detector can be performed with a view to what motions the patient might perform while awake, and which the patient would not perform while unconscious. Moreover, windows of time can be excluded when the compression mechanism is working, and is thus profoundly shaking the patient's body. Same if an auxiliary compression mechanism is also used, as described later in this document.

In some versions, consciousness detector 946 is provided with a clip, adhesive tape, pin, releasable loop of twine or plastic band, or other attaching means for attaching to patient 982. Attachment could be to the patient's abdomen, foot, finger, diaphragm, forehead, ear, etc. In fact, to assist in a more accurate detection of the patient regaining consciousness, the patient may be instructed by a user interface to move their foot or fingers (e.g. "MAKE A FIST!"), as will be described later in this document. The patient would hear such an instruction only while being conscious, etc.

FIG. 10 is a diagram of a patient 1082 with a sample consciousness detector 1046 that includes an electrode according to embodiments. The electrode can be configured to capture an electrical signal of the patient, such as an ECG. Certain features of an ECG, such as a QRS complex can indicate that return of spontaneous circulation (ROSC) has occurred, and therefore compressions may be paused completely!

In some versions, the consciousness detector includes a camera that is configured to capture an image of the patient. Examples are now described.

FIG. 11 is a diagram of a patient 1182 with a sample consciousness detector 1146. Consciousness detector 1146 forms a small housing and has an opening towards the patient's skin. A light inside the housing illuminates the patient's skin. A camera inside the housing, images the patient's skin from a short distance. The skin color or pallor can indicate circulation, while compressions are taking place and while not. Consciousness detector 1146 can be attached to the patient's skin, avoiding the clothes, for example with a rubber band around an extremity.

FIG. 12 is a diagram of a CPR system 1200 that has a retention structure 1240 for a patient 1282. CPR system 1200 has a compression mechanism 1248, and a consciousness detector 1246 that includes a camera. The camera can be implemented as described in copending U.S. patent application Ser. No. 14/642,027. In such embodiments, then, the camera of consciousness detector 1246 is configured to capture and analyze images of patient 1282. These images can be analyzed for evidence of waking up, such as motion of the eyes, change of the patient's place between the compressions, etc.

Figure 24:
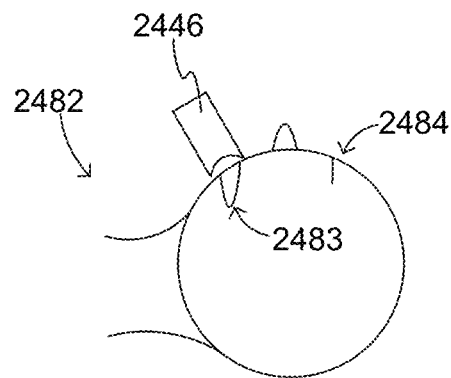
FIG. 24 is a diagram of a sample sensor being implemented by a ventilator according to embodiments.

In other versions, a consciousness detector may be implemented by monitoring of respiratory parameters, such as airway pressure. An example is shown in FIG. 24.

Above, and with reference to FIG. 8, it was described how the processor can slow down the compressions automatically, so as to increase the patient's comfort. The reverse can also be true, especially if it is deemed that the patient's long term well-being cannot afford too much time in the slower frequency. An example is now described.

Referring again to FIG. 4, in some versions processor 442 can be configured to operate in at least one of a normal mode 452 and a tranquil mode 454. In some versions, while processor 442 operates in normal mode 452, it is configured to control compression mechanism 448 to perform the compressions at an average frequency of at least 64 cpm for a time interval of at least 15 sec. In some versions, while processor 442 operates in tranquil mode 454, it is configured to control compression mechanism 448 to perform the compressions at an average frequency between 0.5 cpm and 64 cpm for a time interval of at least 15 sec. In such embodiments, processor 442 can be further configured to automatically revert to operating in the normal mode, responsive to having operated in the tranquil mode for a threshold time duration. This can be useful in the event of a rescuer who is poorly instructed or distracted.

The threshold duration can be, for example 1 minute. In addition, the threshold duration may be affected by other factors, such as vital signs of the patient, how long the patient was unconscious before CPR system 400 was applied to them, and how well optimized were the compressions during the tranquil mode—the more optimized, the higher the tolerance for a longer tranquil mode. Accordingly, a score can be kept as to how much, and for how long there was underperformance; when that score reaches a threshold, the CPR system could return to normal mode. In addition, after the patient is sedated, the patient may be able to tolerate longer intervals of normal mode while conscious.

In embodiments, CPR system 400 is further able to find an optimal frequency for chest compressions in tranquil mode 454. Such an optimal frequency would maintain the patient unconscious, while being as high as possible, to maintain as much circulation as possible. Examples are now described.

Figure 13:
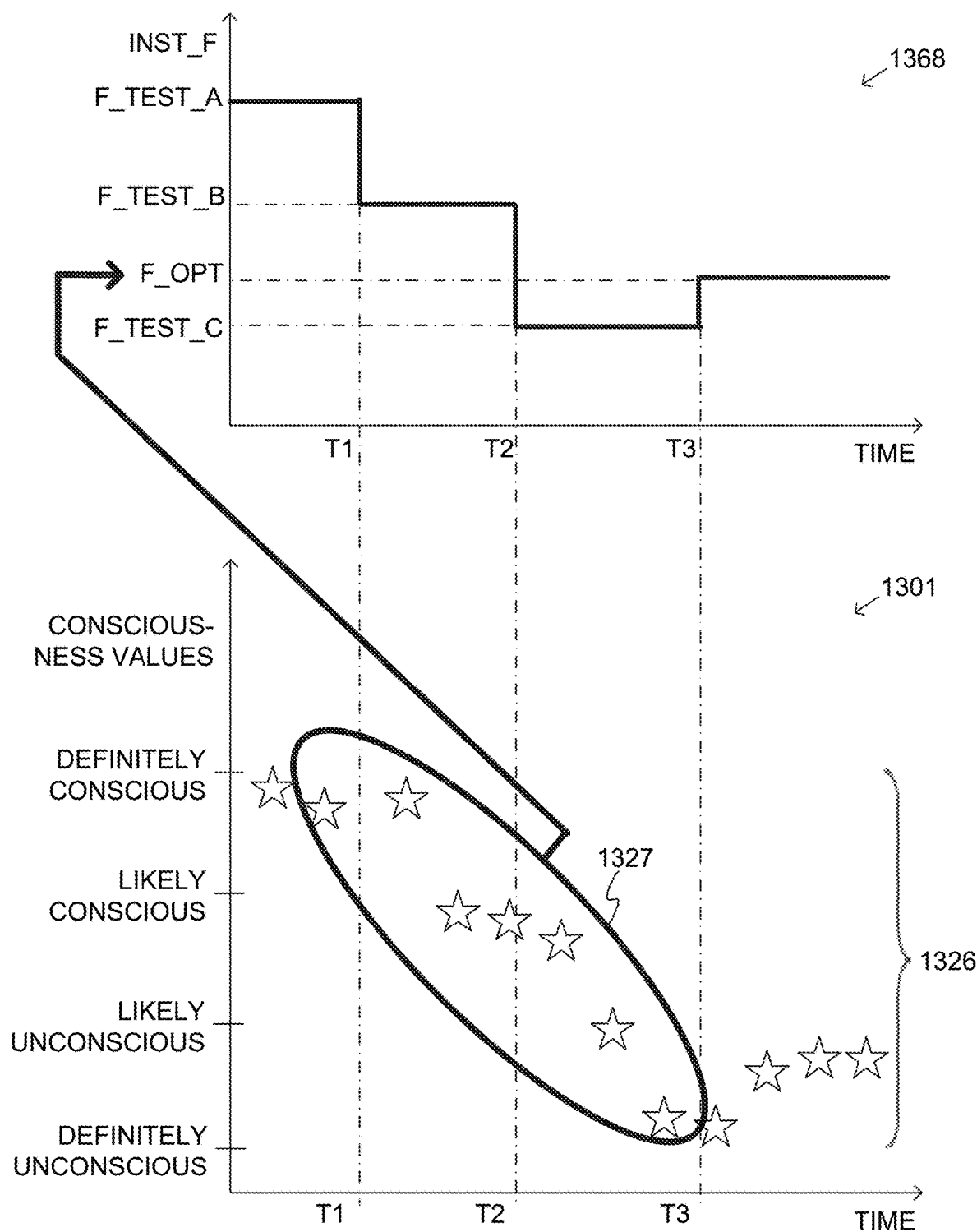
FIG. 13 shows a combination of a time diagram illustrating how an instantaneous frequency of chest compressions performed as a test in search of an optimal frequency can change before the optimal frequency is determined and adopted, along with a time diagram of a sample series of outputted consciousness values that result from the test and inform the determination of the optimal frequency.

FIG. 13 shows a combination of a time diagram 1368 and a time diagram 1301, whose horizontal time axes are aligned. These diagrams of FIG. 13 are related in nature, but not exactly aligned in purpose, with the diagrams of FIG. 8.

In diagram 1368, a time evolution is shown of an instantaneous frequency INST_F of the performed chest compressions. These compressions can be characterized as test compressions. Different instantaneous frequencies can be tried for the test compressions; in other words, processor 442 is configured to control compression mechanism 448 to perform test compressions such that time spacings between successive ones of the test compressions have at least two different values.

In the example of diagram 1368, the instantaneous frequency INST_F starts at F_TEST_A for some time until time T1, then is reduced to F_TEST_B for some time until time T2, and then reduced further to F_TEST_C for some time until time T3. Test compressions are thus tested for three frequencies, while only two need be used. It will be recognized that, in the example of FIG. 13 one starts with a conscious patient, and the test compressions are such that some of the time spacings increase with time. Equivalently, one could start with an unconscious patient, and increase the test frequencies. In such cases, the test compressions are such that some of the time spacings decrease with time.

In diagram 1301, resulting consciousness values 1326 are shown. A subset of consciousness values 1326 before time T3 can be characterized as test consciousness values 1327. These are similar in nature to consciousness values 826, but their purpose is testing.

In versions, then, processor 442 can be further configured to determine an optimal frequency F_OPT from at least some of test consciousness values 1327. Indeed, values 1327 inform when various thresholds are crossed, both with their values and their delay in timing from when the instantaneous frequency changed. It should be appreciated that the optimal frequency F_OPT may vary widely between individual patients of different physical characteristics and physiologies. Moreover, in addition to the computation of F_OPT, a computation may become available for how long F_OPT may be used, before having to revert to the normal mode.

Once optimal frequency F_OPT is determined from test consciousness values 1327 of diagram 1301, its value can be placed on the vertical axis of diagram 1368, as shown by a bold arrow in FIG. 13. At time T3, then, in diagram 1368, the optimal frequency F_OPT may become adopted as the instantaneous frequency for some time. In other words, when operating in tranquil mode 454, processor 442 can be configured to control compression mechanism 448 to perform the compressions at the optimal frequency for at least 15 sec, 30 sec, 45 sec or even longer, for first time interval 410 second time interval 420, etc. Plus, during that time one may deviate from the optimal frequency, for example by plus or minus a percentage such as 20%.

Those consciousness values 1326 that occur beyond time T3 then are, strictly speaking, no longer test values. It would be advisable, however, to monitor them for a long term trend, perhaps adjusting F_OPT, etc.

It will be further recognized that, in some versions, the time from T3 and beyond could be time interval 410. In other words, time interval 410 need not be the beginning of the event, but instead be a prolonged time where compressions are delivered and the patient is tranquil.

Returning to FIG. 4, versions described above are where CPR system 400 of FIG. 4 may change its operation autonomously, automatically, even if the rescuer does nothing. This may help where a rescuer is inexperienced, the rescue team is small, and/or where a medical director demands consistent treatments.

In some versions, CPR system 400 also includes a user interface 404. User interface 404 can be configured to be operatively coupled with processor 442, whether by direct wiring or via a communication link between a communication module of CPR system 400 (not shown) and that of a mobile device, such as a tablet, mobile phone, laptop, etc., which implements the user interface.

User interface 404 can be configured to receive one or more control inputs from a human. It will be appreciated here that the human is the rescuer although, in some versions, the human can be the patient who at the time is receiving chest compressions. In any event, an attentive and experienced rescuer may exercise as good or even better judgement in making decisions than allow the CPR system to execute preprogrammed protocols.

In such versions, processor 442 can be further configured to change, responsive to the control input received via user interface 404, from operating in one of tranquil mode 454 and normal mode 452 to operating in the other. An example is now described.

Figure 14:
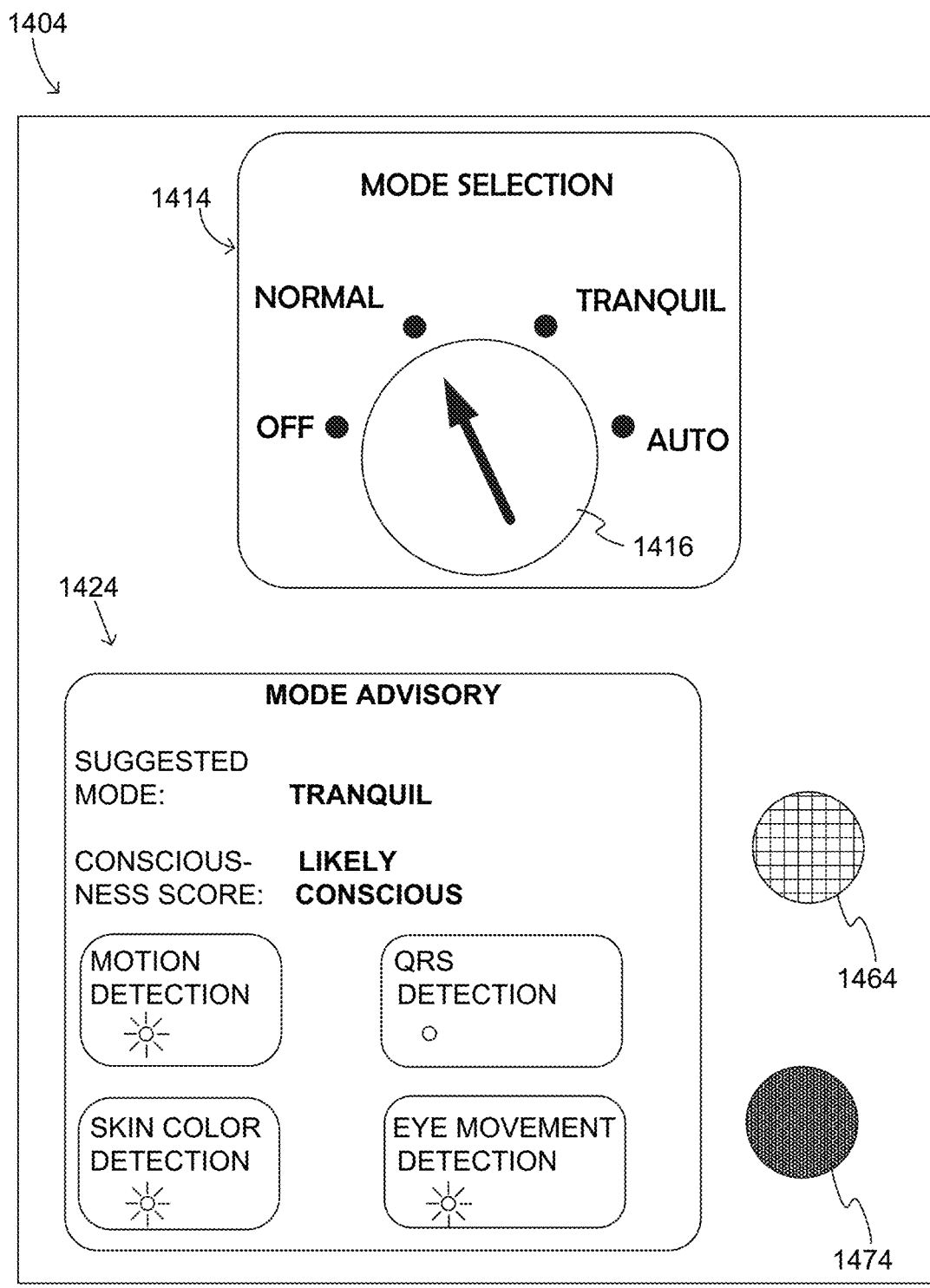
FIG. 14 is a view of a sample user interface made according to embodiments.

FIG. 14 shows a user interface 1404 made according to embodiments. It will be appreciated that user interface 1404, or different versions of it, could be used for different ways of achieving the underperformance. Sections of user interface 1404 may be implemented on a panel located on retention structure 440, on a screen such as a touch screen, and so on.

User interface 1404 has a mode selection section 1414. Section 1414 has a rotatable selector 1416 that has various settings. Given these settings, section 1414 presents the rescuer with an OFF option for the system, and an AUTO option, by various settings of selector 1416. Aspects of the AUTO option were described above, and may permit the CPR system to operate autonomously. For example, the AUTO mode may implement the tranquil mode while it is deemed tolerable to maintain the patient, and the more effective normal mode otherwise. The AUTO mode may also implement the optimization feature of FIG. 13 to find F_OPT and other parameters, and then settle there, or vary some beyond that, etc. In addition, while the AUTO mode is implementing the tranquil mode, other or additional parameters of the waveform could be adjusted for the underperformance as described below for the exclusively tranquil mode.

Furthermore, in section 1414 rotatable selector 1416 presents the rescuer with the option to select an exclusively NORMAL mode or an exclusively TRANQUIL mode, each of which may disable the other modes. Selector 1416 may thus provide the control input by the user. In the TRANQUIL mode the frequency or rate can become smaller as described above, but also other parameters of the waveform could be adjusted for the underperformance. For example the duty ratio, the compression depth, the compression waveform time derivatives, etc. could also be adjusted.

User interface 1404 also has a mode advisory section 1424 for the rescuer. Section 1424 has displays for the shown fields of suggested mode, consciousness score, and possibly others. In addition, it has alerts for four individual consciousness indicators, namely MOTION DETECTION, QRS DETECTION, SKIN COLOR DETECTION and EYE MOVEMENT DETECTION. Of these, all are shown as lit, meaning detecting, except the QRS detection. While only four possibilities are shown in this example, many others exist that could be implemented in versions, such as end-tidal CO2, regional oximetry, EEG, etc.

In section 1424, the computed consciousness score is LIKELY CONSCIOUS, and is an aggregate score. Where, as here, multiple consciousness detectors are available, an aggregate score may be computed from their outputs. The individual outputs on user interface 1404 can further help the rescuer assess whether a sensor has fallen off, is not working, etc.

In section 1424, the suggested mode is TRANQUIL. Upon seeing this, the rescuer may turn selector 1416 to TRANQUIL or AUTO.

In some embodiments, voice commands are also accepted. Examples are now described.

Referring again to FIG. 4, CPR system 400 may also optionally include a voice recognition module (VR) 405. Voice recognition module 405 may be implemented in any way known in the art, such as within processor 442, or within UI 404. In the latter case, module 405 may be embedded in a tablet, mobile phone, etc. at the time of manufacture.

In such versions, user interface 1424 may include a microphone 1474. Microphone 1474 can be configured to capture a sound as the control input of user interface 1424. In such versions, voice recognition module 405 can be configured to recognize whether or not the sound captured by microphone 1474 resulted from a preset utterance, which could be a recognizable command. If voice recognition module 405 indeed recognized the captured sound as having resulted from the preset utterance, processor 442 can be further configured to change from operating in one of tranquil mode 454 and normal mode 452 to operating in the other.

In some versions, as in the example of FIG. 14, user interface 1404 further includes a speaker 1464. Speaker 1464 can be configured to speak an instruction to the patient. The instruction can be to vocalize the preset utterance, if the patient is unbearably uncomfortable. For example, the instruction can be: "IF YOU CAN'T TAKE IT SHOUT: STOP". In such versions, the spoken command "STOP" can be accepted as a valid command for reverting to the tranquil mode. If the CPR system deems that the tranquil mode is not available, the instruction need not be spoken to the patient, of course.

Returning to FIG. 4, embodiments may also benefit from what is described later in this document. For example, embodiments may include auxiliary compression mechanisms, and so on.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc. These algorithms are not necessarily purely mathematical, and are configured to address challenges particular to the problem solved, as will be apparent to a person skilled in the art. In embodiments, a non-transitory computer-readable storage medium 441, 1741 stores one or more programs which, when executed by systems or devices according to embodiments, result in operations according to embodiments. Execution can be by a processor 442, 1742 that reads the storage medium, etc.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Methods are now described.

Figure 15:
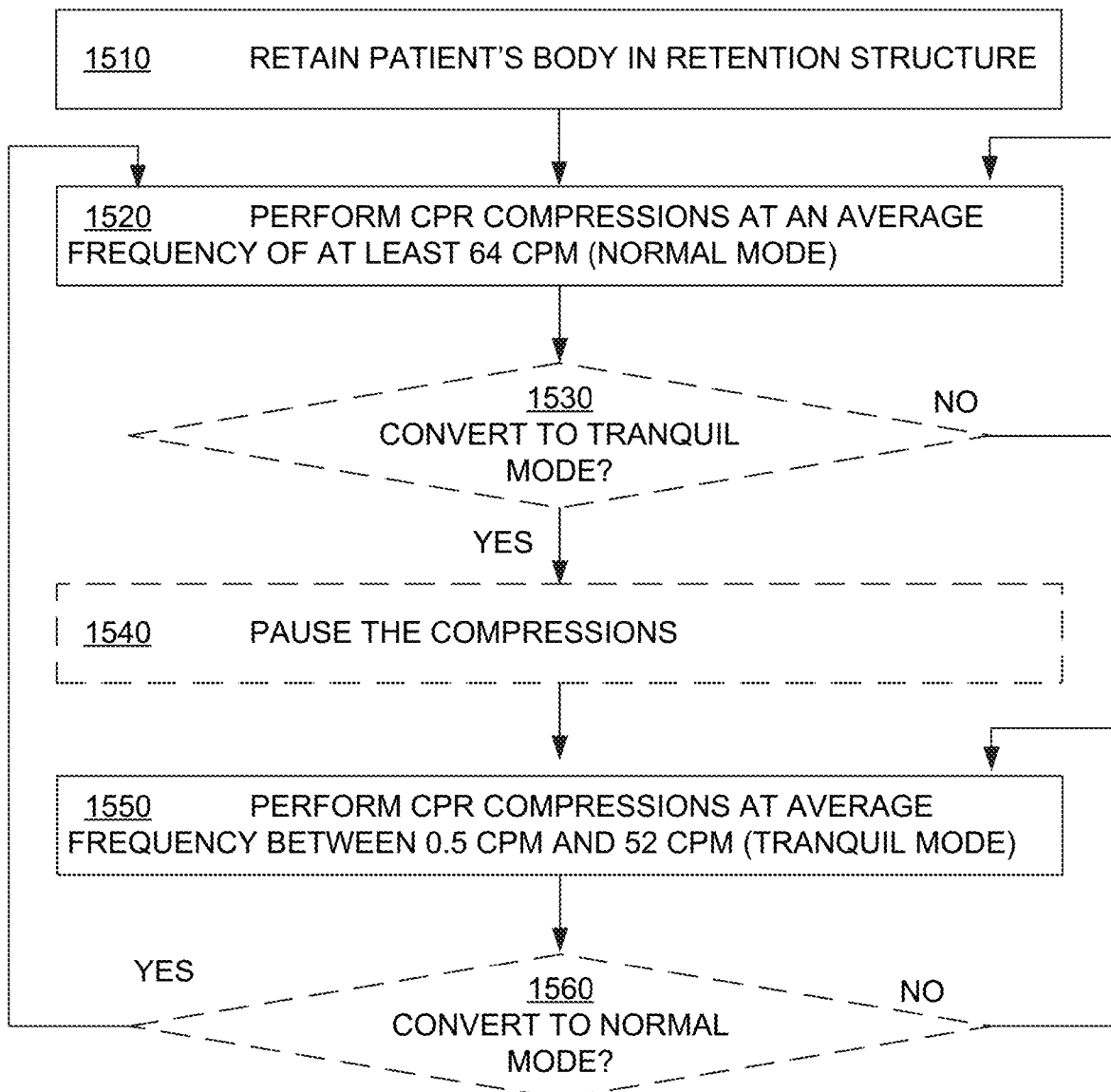
FIG. 15 is a flowchart for illustrating methods according to embodiments.

FIG. 15 shows a flowchart 1500 for describing methods according to embodiments. According to an operation 1510, a body of the patient is retained in the retention structure.

According to another operation 1520, there are performed, while the body is thus retained, automatically CPR compressions alternating with releases to a chest of the body, in which during a time interval other than the first time interval, the CPR compressions are performed at an average frequency of at least 64 cpm. This can also be called operating in the tranquil mode, and the average frequency can even be 100 cpm.

According to another, optional operation 1530, it is inquired whether to convert to the tranquil mode. This operation may be implemented in a number of ways. In some versions, a patient parameter is detected, and a series of consciousness values are output that are determined from the detected patient parameter. The consciousness values may be received, and the answer can be yes if a later consciousness is different from an early consciousness value. In versions, that difference may have to cross a threshold, for example as seen in FIGS. 8 and 13. In some versions the answer is given by a control input that is received from a user interface. If the answer is no, then execution can remain, or revert again to operation 1520.

If the answer is yes, then according to another, optional operation 1540, the compressions are paused temporarily. An example of that was seen in FIG. 8, between times T1 and T2.

Then according to another operation 1550, there are performed, while the body is thus retained, automatically CPR compressions alternating with releases to a chest of the body, in which during a first time interval that lasts 15 sec, the CPR compressions are performed at an average frequency between 0.5 compressions per minute (cpm) and 52 cpm. This can also be called operating in the tranquil mode.

According to another, optional operation 1560, it is inquired whether to convert to the normal mode. This operation may be implemented in a number of ways. One such way is with the consciousness values, as described for operation 1530. In some versions the answer is given by a control input that is received from a user interface. If the answer is no, then execution can remain, or revert again to operation 1550. If the answer is yes, then execution can transfer back to operation 1520, and so on.

Another way for operation 1560 to be answered yes is now described, and involves automatically switching to a normal mode after a threshold time duration has passed. In some versions, CPR compressions are performed automatically at a first average frequency for a time interval of at least 10 sec. The first average frequency can be, for example, less than 90 cpm, and be one where it is known that the patient will remain unconscious. Then CPR compressions may be performed automatically at a second average frequency higher than the first average frequency. The second average frequency could be, for example, larger than 90 cpm, e.g. 100 cpm or even higher. The compressions may be performed at the second average frequency responsive to the CPR compressions having been performed at the first average frequency for a threshold time duration. The compressions may be performed at the second average frequency for a time interval of at least 10 sec, or 45 sec 180 sec or even longer.

Figure 16:
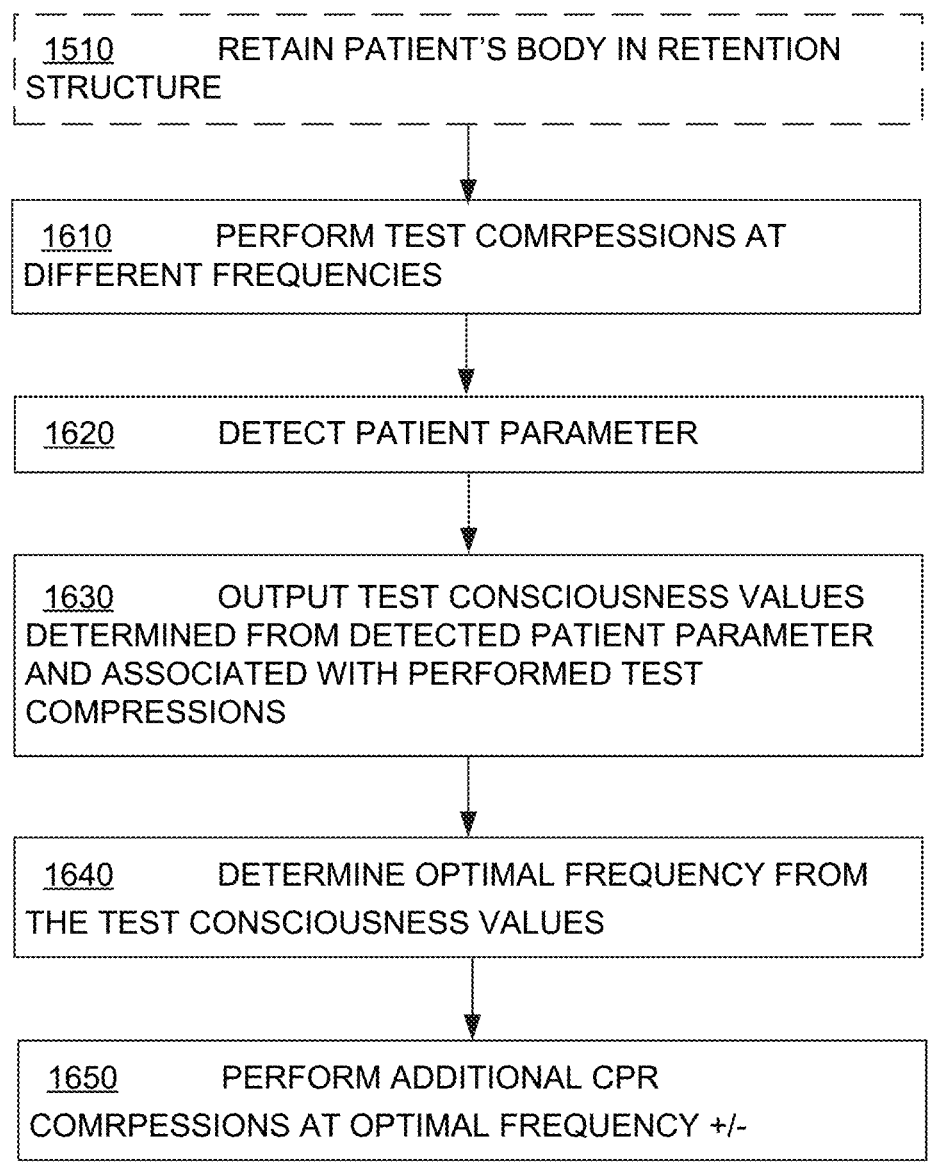
FIG. 16 is a flowchart for illustrating methods for finding an optimal frequency for a tranquil mode according to embodiments.

FIG. 16 shows a flowchart 1600 for describing methods according to embodiments. The methods of FIG. 16 may be performed in addition to those of FIG. 15, and especially for establishing an optimal frequency (rate) F_OPT for operation 1550, or standalone. In some standalone versions, flowchart 1600 starts with the above-described operation 1510.

According to a next operation 1610, test compressions are performed at different frequencies. Such was described with reference to FIG. 13, diagram 1368 above. The frequencies can be increasing, decreasing, etc. Preferably, frequencies used earlier in an event are also used as test frequencies, e.g. by storing their resulting corresponding consciousness values, as test consciousness values, etc.

According to another operation 1620, a patient parameter is detected.

According to another, optional operation 1630, test consciousness values are output, which are determined from the detected patient parameter and are associated with the performed test compressions. Examples of such were seen as values 1327 above.

According to another operation 1640 an optimal frequency can be determined from at least some of the test consciousness values. Such a determination can be elaborate, or simply be the first frequency value that yielded a satisfactory result.

According to another, optional operation 1650, additional ones of the CPR compressions may then be performed in view of the optimal frequency. For example, such additional compressions may be performed at the optimal frequency plus or minus 30% for at least 5 sec, e.g. 15 sec, 60 sec, etc.

Additional, depth-based embodiments are now described in more detail.

Figure 28:
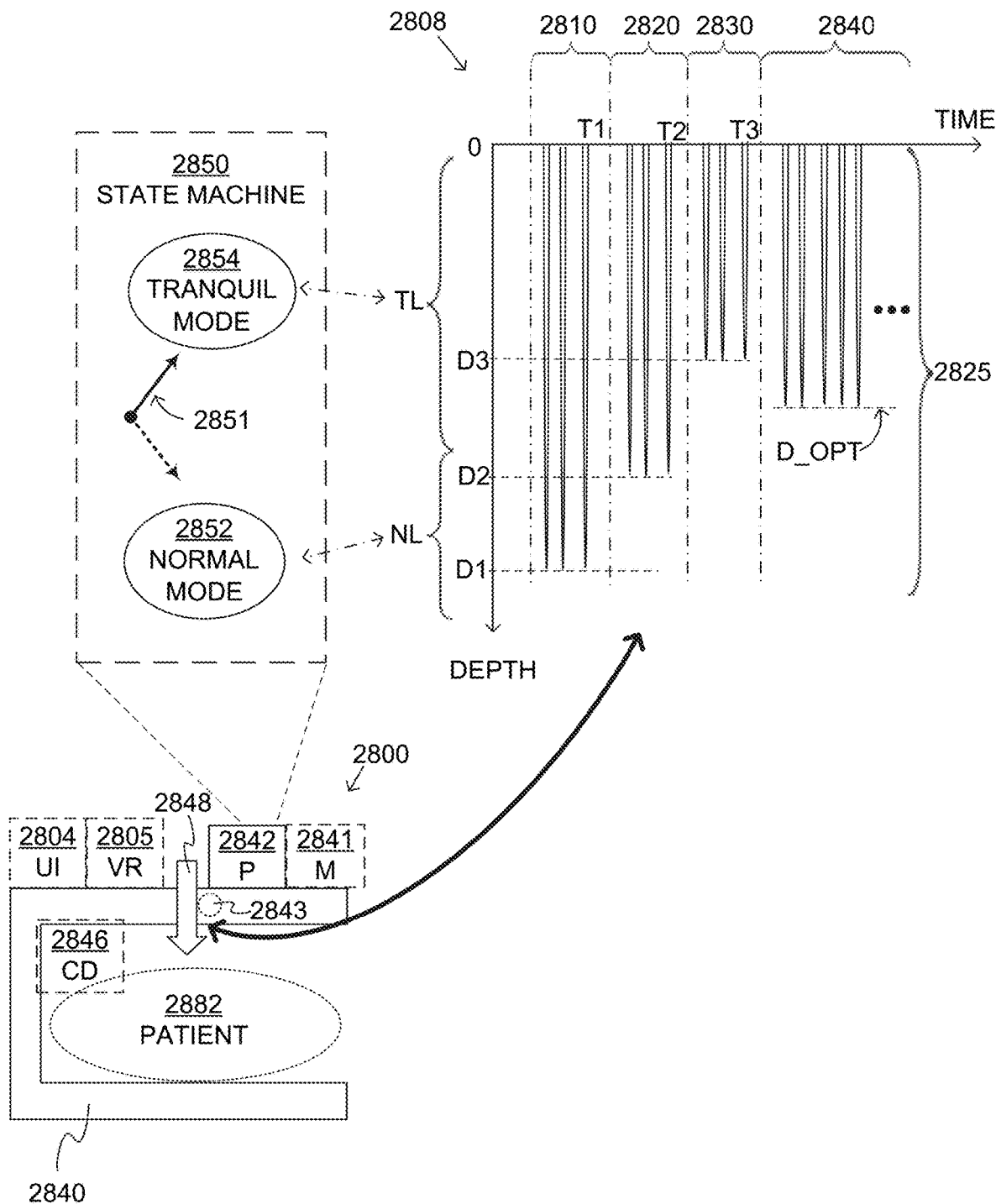
FIG. 28 is a diagram showing an aspect of a sample conceptual CPR system made according to depth-based embodiments, in combination with cooperating aspects illustrating operations of the CPR system according to related embodiments, where test compressions are performed in search of an optimal depth, and then where the optimal depth is determined and adopted.

FIG. 28 is a diagram of an aspect of a conceptual Cardio-Pulmonary Resuscitation (CPR) system 2800, in combination with a cooperating aspect 2808 that illustrates rate-based embodiments of CPR system 2800.

CPR system 2800 is usable by a rescuer (not shown) to care for a patient 2882. Much of the description of CPR system 400 applies also to CPR system 2800, including a retention structure 2840, a compression mechanism 2848, motor 2843, a processor (P) 2842, an optional memory (M) 2841, a User Interface 2804, an optional voice recognition module (VR) 2805 and one or more consciousness detector 2846.

In some versions, processor 2842 is capable of operating in different modes. In the example of FIG. 28, at least a normal mode 2852 and a tranquil mode 2854 are possible. In some versions, processor 2842 includes a state machine 2850, and is able to choose its mode of operation by a selector 2851. In the example of FIG. 28, selector 2851 has selected tranquil mode 2854.

Processor 2842 can be configured to control compression mechanism 2848 to operate in certain ways according to embodiments. Of course, where motor 2843 is used, processor 2842 can be configured to control compression mechanism 2848 by controlling the operation of motor 2843.

In some versions, the depth of the compressions is reduced, so as to accomplish the underperformance. In particular, aspect 2808 is a time diagram of compressions 2825. In aspect 2808, time is depicted in the horizontal axis while depth is depicted in the vertical axis, increasing in a downward direction. Some sample compressions 2810 are shown being performed up to a first time T1, then more compressions 2820 for up to a second time T2, then even more compressions 2830 for up to a third time T3, and then even more compressions 2840 thereafter. Compressions 2825 are shown generically as to their timing and shape, in the sense that they could have any duty ratio and their individual downward waveforms could have any shape.

In aspect 2808, compressions 2810, 2820, 2830 can be characterized as test compressions, reaching test depths D1, D2, D3 respectively. The pattern of aspect 2802 need not be followed exactly; fewer than three test depths may be tested, in search of the optimum depth D_OPT. In addition, the test compressions at each test depth need not be 3 as shown in sample aspect 2808.

In aspect 2808, similarly with FIG. 13, consciousness detector 2846 can be configured to detect a patient parameter, and to output a first test consciousness value, a second test consciousness value, a third test consciousness value, etc. These test consciousness values may be determined from the detected patient parameter, and corresponding respectively to first test depth D1, second test depth D2, third test depth D3, etc.

In such versions, processor 2842 can be further configured to determine an optimal depth D_OPT from the test consciousness values, and to control compression mechanism 2842 to then perform additional CPR compressions 2840 at the optimal depth D_OPT plus or minus 30% for 5 sec, 15 sec, 60 sec, or longer.

In this example, the first test depth D1 is larger than the second test depth D2. Equivalently, the first test depth could be smaller than the second test depth. Plus, the optimal depth can be the last test depth that was tried, i.e. D2, D3, etc.

Figure 29:
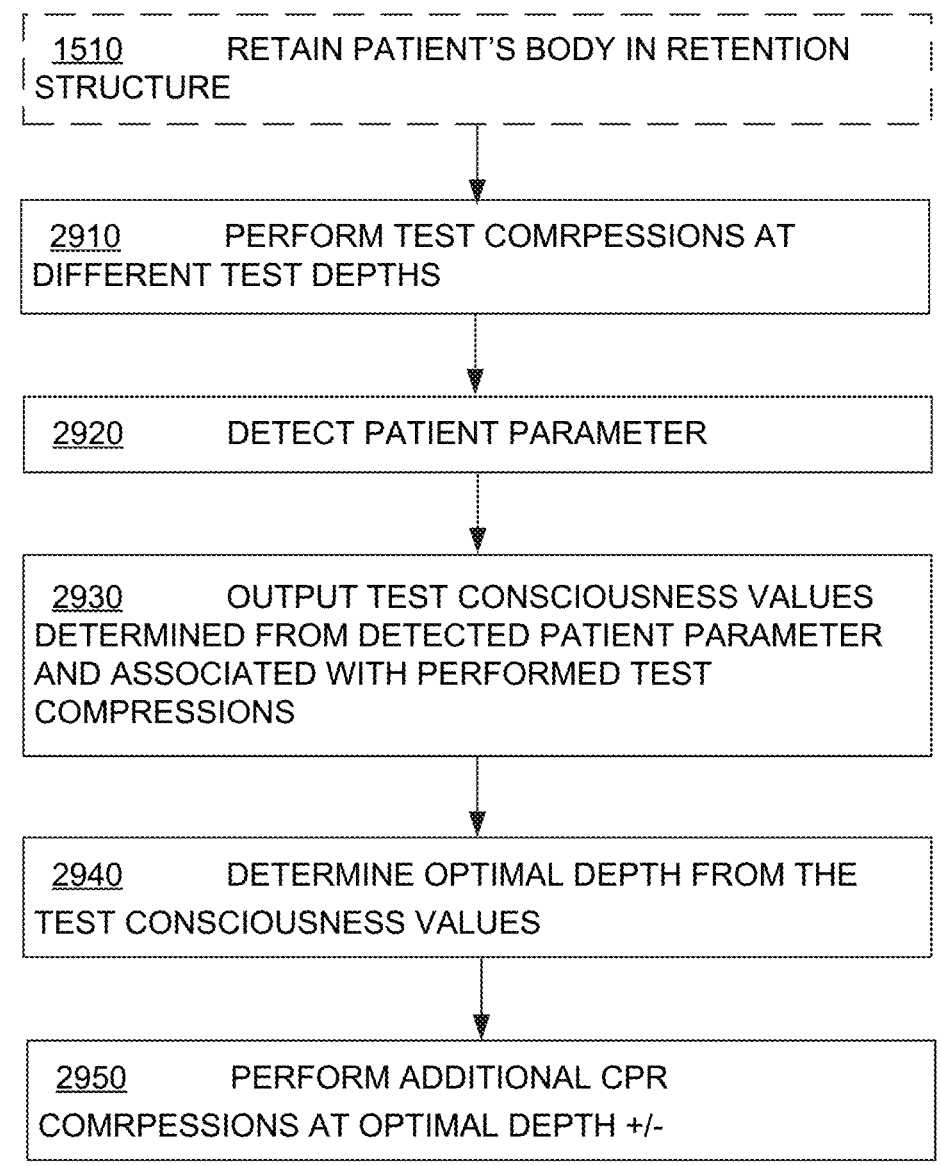
FIG. 29 is a flowchart for illustrating methods for finding an optimal frequency for a tranquil mode according to embodiments.

FIG. 29 shows a flowchart 2900 for describing methods according to embodiments. In some standalone versions, flowchart 2900 starts with the above-described operation 1510.

According to a next operation 2910, test compressions are performed at different test depths. Such was described with reference to FIG. 28, aspect 2808 above. The test depths can be increasing, decreasing, etc. Preferably, depths used earlier in an event are also used as test depths, e.g. by storing their resulting corresponding consciousness values, as test consciousness values, etc.

According to another operation 2920, a patient parameter is detected.

According to another, optional operation 2930, test consciousness values are output, which are determined from the detected patient parameter and are associated with the performed test compressions.

According to another operation 2940 an optimal depth D_OPT can be determined from at least some of the test consciousness values. Such a determination can be elaborate, or simply be the first depth value that yielded a satisfactory result.

According to another, optional operation 2950, additional ones of the CPR compressions may then be performed in view of the optimal depth. For example, such additional compressions may be performed at the optimal depth plus or minus 30% for at least 5 sec, e.g. 15 sec, 60 sec, etc.

In additional versions of the invention, the chest compressions could be varied during the process of CPR. They could be varied continuously. Some previously suggested variations describe two or three different distinct types of chest compression patterns that comprise a "cycle" of some duration. The different cycles are repeated in some sequence to deliver chest compressions which vary over time but have some repetitive pattern. In another embodiment, n (where n=1:∞) distinct types of chest compression patterns can exist, which can be repeated or not repeated in any permutation. In another embodiment the chest compression parameters that are varied (i.e., rate, depth, pauses, release velocity, compression velocity) would be varied continuously in some way. In one embodiment the parameter(s) could be varied continuously in monotonic increasing or decreasing patterns over time. For example, the rate would continuously increase or decrease. In another embodiment the chest compression parameters would be generated randomly within predefined limits (FIG. 2c). In another embodiment the chest compression parameters may change in a non-monotonic fashion during the time course of CPR.

In additional versions of the invention, the compression velocity and the release velocity could be varied. One embodiment is a mechanism and method to control a mechanical CPR device to provide chest compressions in which the rate a chest compression is performed and the rate at which the compressed chest is decompressed can be adjusted over time to optimize hemodynamics for different parts of the body or for improved hemodynamics overall. In on embodiment the chest decompression is passive, in another the decompression is active (i.e., facilitated by a mechanism such as a suction cup or adhesive pad). In another, the chest compression release velocity is adjustable with an adjustable final position above the normal chest height following recoil from the previous compression.

In additional versions of the invention, a chest compression pattern may facilitate diagnosis. Time-varying chest compressions can be adjusted to facilitate use of technologies to visualize and interpret the underlying ECG waveform in the presence of chest compression artifact. In one embodiment the compression parameters will remain constant for a set period of time so as to allow a filtering technology to be used on a monitoring device (such as a LIFEPAK15®, etc.) to display ECG without chest compression artifact and either allow the monitor device or the care provider to make an assessment as to the shockability of the underlying rhythm. In another embodiment, the chest compression device could send a signal to the monitoring device indicating the compression parameters where the monitoring device could use that information to adjust filtering parameters to exclude chest compression artifact under varying compression parameters.

In another embodiment the chest compression pattern would include a brief pause and during which time patient monitoring devices would make measurements, report values, and/or make a treatment decision based on the presence of return of spontaneous circulation (ROSC). Monitoring techniques would be combined with the interpretation of the ECG signal and include: ultrasound imaging for detection of cardiac wall motion, heart valve motion or brain markers (EEG, oximetry and more), blood flow in other parts of the body; video or photograph based assessment of skin pallor; and auscultative techniques for detecting blood flow or heart sounds. If ROSC is detected chest compressions are stopped, if ROSC is not detected chest compressions resume.

In additional versions of the invention, chest compressions could be varied during the process of CPR for other reasons. For example, heart filling and emptying can be optimized cyclically and not just to optimize blood flow to specific organs like heart, lung, or brain. In versions, long (60, 70, 80% compressions duty cycle with or without rate adjustment) compressions may facilitate a longer period for blood ejection, while long (60, 70, 80% decompressions duty cycle with or without rate adjustment) decompressions may facilitate a longer period for heart filling.

In additional versions of the invention, chest compressions may be periodically slowed to facilitate better ventilation. A synchronization signal may be sent to a ventilator device or feedback device (for ventilation prompts during bag mask ventilation) to improve timing and provide better ventilation (with lower airway pressures, higher TD volume) during the prolonged decompression phases of chest compressions.

In additional versions of the invention, as chest compressions become time varied, temporary changes in compression parameters peri-shock can be used to avoid difficulties with coordinating with shocking, and thus facilitate defibrillation. There is currently a scientific debate concerning continuous chest compressions during defibrillation. It has been suggest that providing chest compressions during defibrillation decreases shock success, still others suggest that chest compressions shortly after defibrillation may reinitiate fibrillation. On the other hand, stopping chest compressions peri-shock has been shown to be detrimental for patient survival (although this is likely true for chest compression pauses other than peri-shock pauses). The risk can be reduced, however, by synchronizing a chest compression device with a defibrillator as follows: the chest compression pattern could be altered to not-compress the chest during the vulnerable time periods while minimizing or eliminating pauses by utilizing a compression waveform optimized for a specific purpose (such as optimal heart filling) peri-shock.

In additional versions of the invention, chest compressions could be varied during the process of CPR to minimize injury while maintaining acceptable blood flow. Or, if optimal hemodynamics can be achieved at a wide range of chest compression parameters the parameters would then be narrowed further with the goal of simultaneously maximizing blood flow and minimizing such injury. This embodiment should be combined with the possibility of targeted maximization of blood flow to specific organs as well as overall cardiac output.

In additional versions of the invention, time varying chest compressions can be combined with additional technologies and therapies designed to improve CPR, for example: ventilations synchronized with chest compressions or Intermittent Positive End-Expiratory Pressure Ventilation.

The proposed solution is to perform intermittent positive end-expiratory pressure ventilation (PEEP). As the chest compressions are varied over time, alveolar recruitment maneuvers may automatically (or manually) become synchronized with chest compressions. For example, if the chest compression pattern includes slow compression rates, intermittent PEEP could be performed between compressions. Alternatively, the chest compression pattern may include pauses or prolonged decompression during which time PEEP could be delivered. The idea is to synchronize the PEEP delivery through feedback from the chest compression device and automatically perform the ventilations at the right time to optimize re-recruitment of alveolar tissue. Alternatively the feedback from a chest compression device could be used to control an indicator that would convey timing information to a human care provider doing ventilation manually by bag mask ventilation or a manual driven ventilator.

As background for PEEP, during CPR, $CO_2$ ventilation and $O_2$ delivery are important aspects of achieving positive outcomes for the patient. While achieving optimal blood flow is critical for this process, the lungs play a key role by providing the mechanism of gas exchange between the ventilated air and the blood. During CPR, chest compressions cause significant formation of atelectasis in the lung alveoli. This means the alveoli, the small sacks of lung tissue in which gas exchange occurs, are collapsed and can no longer exchange gases. A treatment to minimize and re-recruit alveolar tissue into this process can be positive end-expiratory pressure ventilation (PEEP). Unfortunately during chest compressions, PEEP can be detrimental as chest compressions increase intrathoracic pressure and reduce venous return to the heart. The embodiments described above, however with intermittent PEEP can overcome this.

In additional versions of the invention, time varying chest compressions can be combined with additional technologies and therapies designed to improve CPR, namely for timing mechanisms for pharmacological treatments. Embodiments include a mechanism and method for controlling the timing of pharmacological agent administration which can be performed either automatically or manually. As such, the timing mechanism should include a control mechanism and automatic delivery mechanism or indicator mechanism to communicate timing to a user. The timing of pharmacological agent administration would be dependent on the administered agent and its intended purpose and its relationship to the time varying chest compressions. For example, if the chest compression parameters are cycling between values optimized for systemic flow and values optimized for cerebral flow and epinephrine is going to be the delivered compound, the delivery timing could be controlled such that delivery occurs during compressions optimizing systemic flow. The purpose may be to preferentially deliver epinephrine to the systemic blood vessels to induce vasoconstriction while reducing vasoconstriction in the brain, with the end result being enhanced blood flow to the brain. As background of the above, an important consideration during CPR is the delivery of pharmacological agents to the patient to promote better outcomes. Commonly used agents include vasoactive and anti-arrhythmic drugs and sometimes sedatives.

In additional versions of the invention, time varying chest compressions can be combined with additional technologies and therapies designed to improve CPR, namely an impedance threshold device (ITD). Intrathoracic pressure is an important determinant of venous blood return during CPR. The impedance threshold device (ITD) is designed to decrease intrathoracic pressure during the decompression phase of CPR chest compressions. The ITD works by means of a pressure release valve preventing, until a certain pressure threshold is reached, air flow back into the lungs during the decompression. The decreased intrathoracic pressure creates a suction mechanism drawing blood back towards the heart through the venous system. The ITD could be combined with time varying chest compressions to enhance the desired effects of time varying compressions by being switched on or off. In the on mode, inward airflow would be limited based on pressure threshold and in the off mode, airflow would be allowed to freely pass through the device. For example, if the goal of the time varying compressions was to alternate between optimal cerebral blood flow and optimal pulmonary blood flow, the ITD could be turned on to increase pulmonary flow, and off to increase cerebral blood flow. This might work by increasing venous return and RV ejection volume consequently leading to greater pulmonary flow when the ITD is turned on and chest compression optimized for RV filling are performed. On the other hand, when the ITD is turned off, cerebral blood flow would be enhanced by performing brain flow optimized chest compression and reducing RV filling leading to lower central venous presser and hence increasing the cerebral perfusion pressure.

In additional versions of the invention, time varying chest compressions can be combined with additional technologies and therapies designed to improve CPR, namely horizontal acceleration CPR. In embodiments, the patient would be subjected to oscillating horizontal accelerations in the supine position as an alternative to or in combination with chest compression based, or load distributive band based CPR. This type of CPR is referred to as pGz CPR. While the mechanism by which pGz CPR is not well understood, there is evidence that it stimulates endothelial cells which release factors that cause vasodilation. The horizontal accelerations could be varied in intensity, duration, direction, etc. in coordination with the varying chest compressions. For example, if optimal cerebral blood flow is desired, horizontal acceleration in the caudal direction could be synchronized in time with chest compressions and could be performed to direct more blood to the brain. Depending on the speed necessary, this can be performed by devices revealed in copending Ser. No. 14/273,593 (and in particular FIGS. its 8A & 8B).

In additional versions of the invention, Time varying chest compressions can be combined with additional technologies and therapies designed to improve CPR, in particular: Enhanced External Counter-Pulsation (EECP). The idea behind EECP is to apply compressions or constrictions at various parts of the body to enhance the effectiveness of CPR. Constrictions are typically applied using inflatable cuffs or garments and are timed aligned in some fashion to chest compressions or intrinsic heart rhythm depending on the patient condition. In embodiments, time varying EECP can be synchronized with time-varying chest compressions. In versions, if the chest compression pattern is alternating between heart filling and heart emptying, EECP could be performed to enhance this effect by having a duty cycle with <50% constriction during heart emptying compressions and >50% during heart filling compressions. In another version, if the time varying compressions are alternating between lung perfusion and brain perfusion, EECP could be implemented to stay constricted to direct flow to the brain or pulse at 90 degree phase shift to enhance blood flow to the lungs. In embodiments, the EECP is varied over time in a way to enhance the intended effects of time varying chest compressions.

In additional versions of the invention, all embodiments presented above could be combined in any permutation, or all be combined together with or without time varying chest compressions. For instance, pGz CPR+ITD+EECP could be synchronized with time varying chest compression to maximize blood flow. This could be achieved by for example, performing cerebral perfusion optimized time varying compressions, constricting the cuffs in EECP, caudal acceleration in pGz, and having the ITD in the off mode. In embodiments, combinations of such interventions can be varied to control the movement of blood within a patient, thereby optimizing blood flow for desired purposes. One such purpose could be achieving tranquility mode without decreasing total blood flow. In one version, blood may be directed from the lungs, to the heart, and to the brain in a cyclical fashion, so as to optimize blood gas exchange, improve the condition of the heart in preparation for successful defibrillation, and keep the brain alive so as to optimize the chance for neurologically intact survival.

Figure 17:
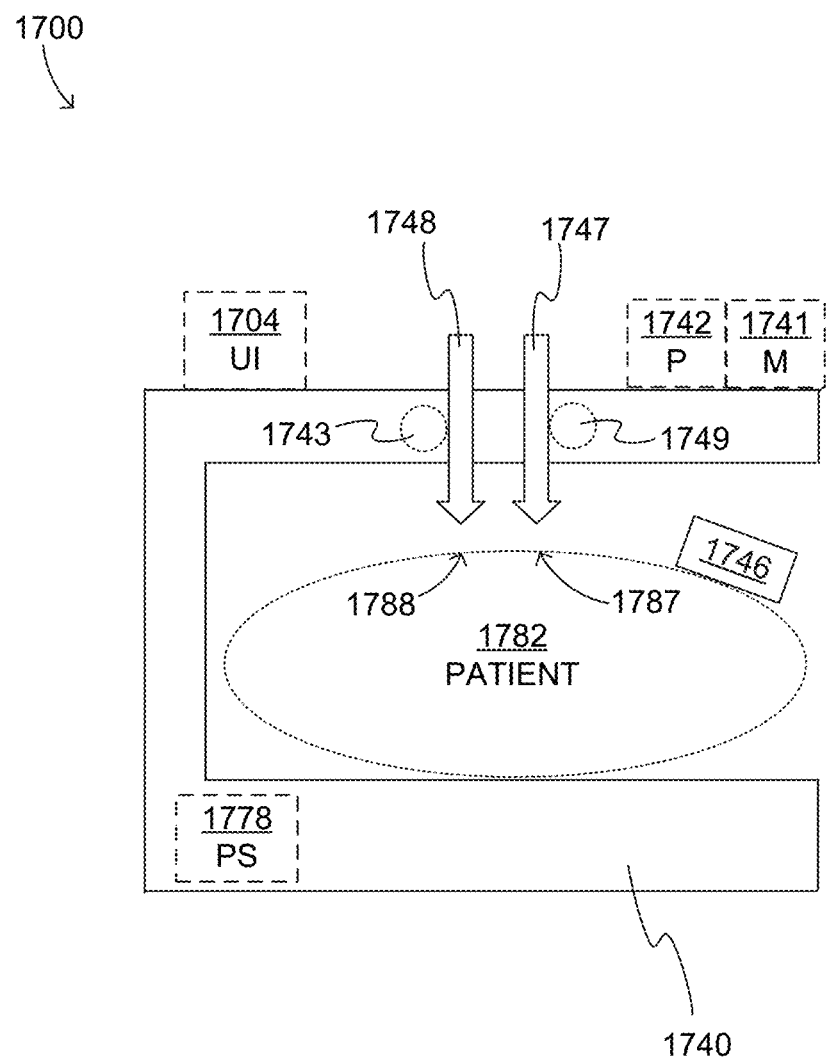
FIG. 17 is a diagram showing a sample conceptual CPR system made according to embodiments.

FIG. 17 is a diagram an aspect of a conceptual Cardio-Pulmonary Resuscitation (CPR) system 1700 according to embodiments. CPR system 1700 is usable by a rescuer (not shown) to care for a patient 1782, similarly for how it was written for CPR system 400.

CPR system 1700 includes a retention structure 1740 that is configured to retain a body of patient 1782. Retention structure 1740 is shown here conceptually, similarly to what was described for retention structure 440.

CPR system 1700 also includes a main compression mechanism 1748 that is attached to retention structure 1740. Again, main compression mechanism 1748 is shown here conceptually, similarly to how compression mechanism 448 was shown. Main compression mechanism 1748 may be implemented similarly to what was described for compression mechanism 448.

Main compression mechanism 1748 can be configured to perform, while the body of patient 1782 is thus retained by retention structure 1740, automatically main compressions alternating with releases to a chest of the body of patient 1782. For example, main compression mechanism 1748 can be driven by a main motor 1743.

These main compressions that are performed by main compression mechanism 1748 are CPR compressions, of the type described for the CPR compressions performed by compression mechanism 448. For example, these main compressions can cause the chest to become compressed by at least 2 cm and possibly deeper, as described for the CPR compressions performed by compression mechanism 448.

CPR system 1700 additionally includes an auxiliary compression mechanism 1747. Auxiliary compression mechanism 1747 is distinct, different from main compression mechanism 1748. Auxiliary compression mechanism 1747 can be coupled to retention structure 1740.

Auxiliary compression mechanism 1747 is configured to perform, while the body of patient 1782 is retained by retention structure 1740, automatically auxiliary compressions alternating with releases to the body. In other words, the body could be receiving main compressions from main compression mechanism 1748, auxiliary compressions from auxiliary compression mechanism 1747, or both. As will be seen later in this document, in some versions, the main compressions can be performed in coordination with the auxiliary compressions for a combined medical effect. This effect can be further propelling the blood, or strategically constricting certain pathways.

In some versions, CPR system 1700 further includes a power supply 1778. Power supply 1778 can be configured to deliver power to both main compression mechanism 1748 and auxiliary compression mechanism 1747.

In some versions, while main motor 1743 is configured to drive main compression mechanism 1748, CPR system 1700 also includes an auxiliary motor 1749 configured to drive auxiliary compression mechanism 1747. In such versions, power supply 1778 can be configured to deliver power to both main motor 1743 and auxiliary motor 1749. In other versions, main motor 1743 is configured to drive both main compression mechanism 1748 and auxiliary compression mechanism 1747.

In some versions, CPR system 1700 further includes a user interface 1704. User interface 1704 can be configured to receive a user input from the rescuer. In such versions, an operation of one of main compression mechanism 1748 and auxiliary compression mechanism 1747 is changed responsive to the user input differently than the other. In other words, the user input can affect the differently, for example only one or the other.

In some versions, auxiliary compression mechanism 1747 is implemented in ways similar to what has been described as possible for main compression mechanism 1748. For example, auxiliary compression mechanism 1747 can include a piston, a belt, and so on. In other words, it is possible that auxiliary compression mechanism 1747 is implemented similarly to, or differently from how main compression mechanism 1748 is implemented.

In other versions, auxiliary compression mechanism 1747 is implemented in other ways, according to what is needed and what can cooperate with main compression mechanism 1748. For example, auxiliary compression mechanism 1747 may include a load-distributing band. Or it may include an inflatable bag, and the auxiliary compressions can be performed by inflating the bag in such a way that, upon being inflated, the bag compresses the patient's body in some way, by constricting blood flow, or against retention structure 1740, etc.

In general, the main compressions could be performed at a first location 1788 of the chest of the patient's body, while the auxiliary compressions could be performed at a second location 1787 of the body. Second location 1787 depends on the application.

In some versions, auxiliary compression mechanism 1747 is intended for CPR, in other words the auxiliary compressions are also CPR compressions, in coordination with the main compressions. In such versions, main compression mechanism 1748 could include a first piston, while auxiliary compression mechanism 1747 could include a second piston. The first and the second pistons could be supported by a portion of retention structure 1740, which could be made as central member 141 or overhanging beam 241.

In addition to pistons, or in lieu of the pistons, load-distributing bands can be used. One or more of these pistons can be combined with a load distributing band, to which the piston can be attached or detached, overlapped or alternated in space, to capitalize on blood flow generated by cardiac compression, and by intrathoracic pressure cycling. Load-distributing bands have the advantage that they emulate better changes in intrathoracic pressure, at least when compared to pistons that emulate cardiac compression better, given that both mechanisms could be at play in generating blood flow.

In such cases, the auxiliary compressions can also be performed to the chest of the body. In such cases, main compression mechanism 1748 and auxiliary compression mechanism 1747 can compress independently of each other, or based on feedback from one another. Accordingly, multiple compression mechanisms may optimize CPR for the multiple system of the heart.

In such cases, first location 1788 could even overlap in part with second location 1787, as both compression mechanisms try to reach the heart, for example the left side and the right side of the heart. If center points could be defined for first location 1788 and second location 1787, then a distance between the center points could be measured along a surface of the patient's body, and such a distance would be of the order of a few centimeters. Both pistons could be vertical, to facilitate filling and emptying of the chambers, or somewhat angled with respect to each other so that they both reach the same area.

An advantage of multiple, i.e. two or more, compression mechanisms is that they may be able to work together with synergies. Because the right and left sides of the heart feed separate circuits, but are ultimately attached, controlling the output of one may dictate characteristics of the output of the second. The output of the right side of the heart (which is determined by its input) may add a variable to the input and subsequent output of the left side of the heart, and vice versa. Therefore, two separate devices may allow for modulation of the inputs and outputs of these systems that one alternating piston cannot offer.

For example, one key question about CPR is whether retrograde flow occurs during the release phase of the compression (or perhaps at a different time, or from different types of compressions). It may also be true that backflow will or will not occur based on the pressure applied to one side of the heart. For example, if the right side of the heart is squeezed and held at the appropriate time, while the left side is continuously pumped with a separate device, it may be feasible to deliver a strong flow in one direction.

Another benefit of having two separate systems can best be illustrated by addressing the left and the right sides of the hearts separately. The chambers on either side have different characteristics, including thicknesses, elasticities, and volumes. The circuits that they feed (pulmonic vs. systemic) have entirely different vascular structures and sizes and consequently resistances, and capacitances. Accordingly, each side could have its own optimal input and resulting output. Therefore, the two sides of the heart may be pumped, even continuously, but with different combinations of patterns as described in previous and current applications.

In addition, the filling of the chambers (atria and ventricle), the rate of the filling, the emptying, and the rate of the emptying, all have implication on blood flow. In a different configuration, where the compression mechanisms are oriented horizontally, they could be used in tandem, similarly as to the description above, in order to facilitate filling and emptying of these chambers.

In some versions, retention structure 1740 includes a back plate that is configured to receive the patient supine. In such versions, auxiliary compression mechanism 1747 is coupled to the back plate, and located such that the auxiliary compressions are performed to an abdomen of patient 1782. In other words, in such versions, second location 1787 is at the abdomen. An example is now described.

Figure 18:
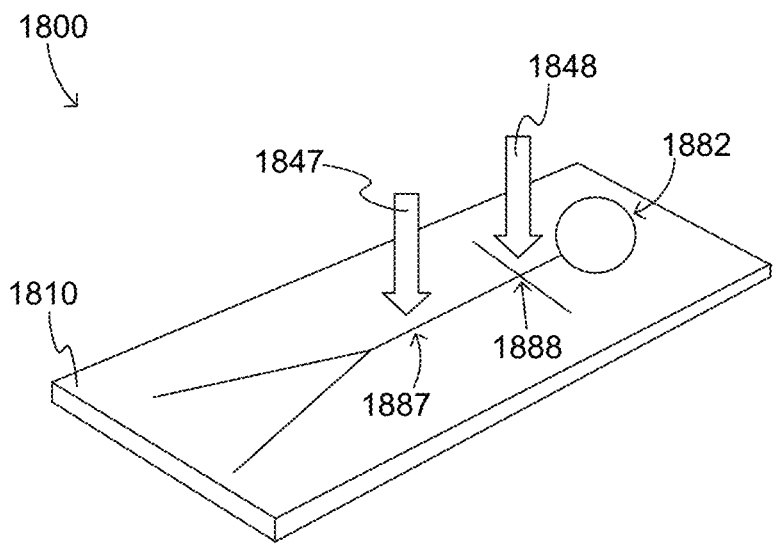
FIG. 18 is a perspective diagram of a sample CPR system made according to embodiments in which the auxiliary compression mechanism compresses an abdomen of the patient.

FIG. 18 is a perspective diagram of a CPR system 1800. CPR system 1800 includes a back plate or platform 1810 that is configured to receive a patient 1882 supine. A main compression mechanism 1848 is configured to perform main chest compressions at a first location 1888 on a chest of patient 1882. An auxiliary compression mechanism 1847 is configured to perform auxiliary chest compressions at a second location 1887 on an abdomen of patient 1882. In this case, the first location 1888 and second location 1887 do not overlap, and are more than a few cm away from each other.

An advantage of multiple compression mechanisms is thus that the abdomen can also be pumped. This is because, although the heart represents the natural pump that supplies blood to the body, during cardiac arrest the heart is no longer an effective pump. Compressions provide an artificial pumping mechanism, but they do not inherently preclude other organs from becoming effective synthetic pumps when compressed.

In CPR system 1800, auxiliary compression mechanism 1847 may be implemented as described above. Two examples are now described in more detail.

Figure 19:
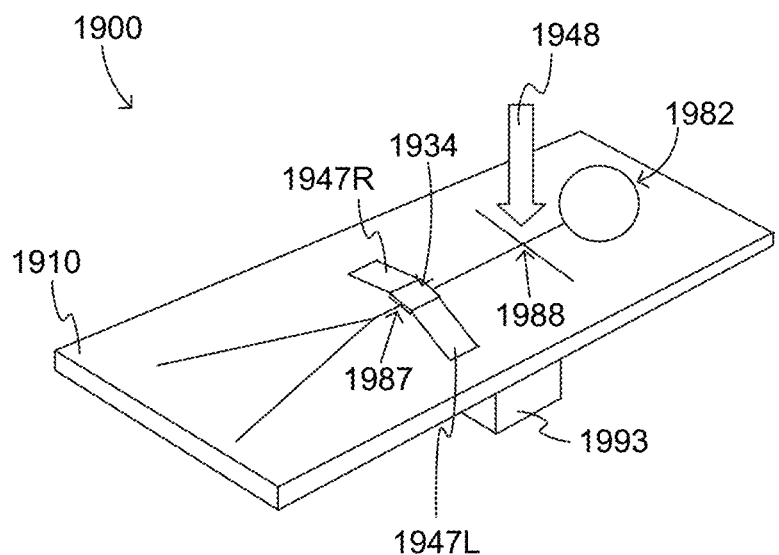
FIG. 19 is a perspective diagram of the CPR system of FIG. 18, made according to a sample embodiment where the auxiliary compression mechanism includes a belt that can be retracted and released by a motor.

FIG. 19 is a perspective diagram of a CPR system 1900. CPR system 1900 includes a back plate or platform 1910 that is configured to receive a patient 1982 supine. A main compression mechanism 1948 is configured to perform main chest compressions at a first location 1988, similarly with FIG. 18.

An auxiliary compression mechanism is also provided, which is configured to perform auxiliary chest compressions at a second location 1987 on an abdomen of patient 1982. In FIG. 19, the auxiliary compression mechanism includes a motor 1993, and a belt that serves as a load-distributing band. In particular, a left side 1947L of the belt has been buckled together with a right side 1947R of the belt by a buckle 1934. Then motor 1993 retracts and releases the buckled belt, so as to constrict and relax the abdomen of patient 1982.

Figure 20:
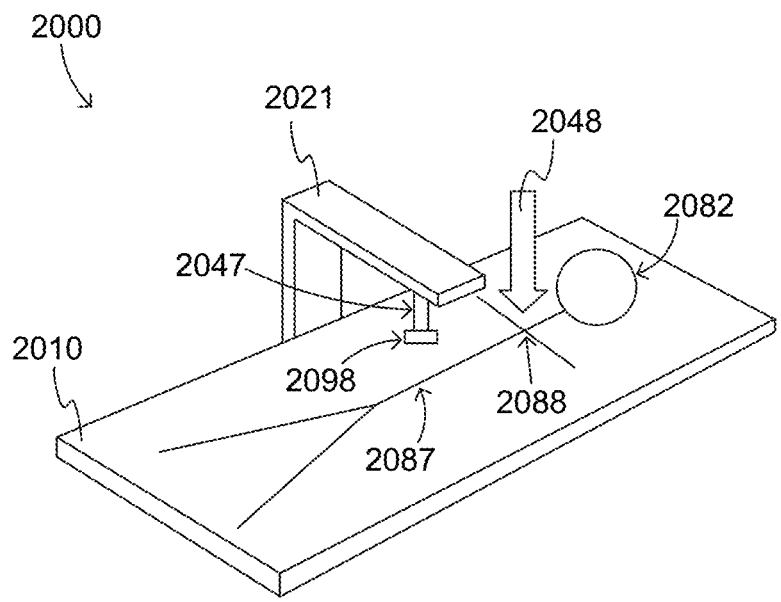
FIG. 20 is a perspective diagram of the CPR system of FIG. 18, made according to a sample embodiment where the auxiliary compression mechanism includes a piston.

FIG. 20 is a perspective diagram of a CPR system 2000. CPR system 2000 includes a back plate or platform 2010 that is configured to receive a patient 2082 supine. A main compression mechanism 2048 is configured to perform main chest compressions at a first location 2088, similarly with FIG. 18.

An auxiliary compression mechanism 2047 is configured to perform auxiliary chest compressions at a second location 2087 on an abdomen of patient 2082. In FIG. 20, the retention structure further includes an arm 2021 configured to become coupled to back plate 2010. Auxiliary compression mechanism 2047 includes a piston that is coupled to arm 2021.

In some of these versions, auxiliary compression mechanism 2047 further includes a suction cup 2098 that is coupled to the piston. Suction cup 2098 can be configured to lift the patient's abdomen during the releases that alternate with the auxiliary compressions. Note that suction cup 2098 is not necessarily similar to suction cup 199 of FIG. 1. Indeed, suction cup 2098 is shaped differently so as to grab and lift the stomach of the patient. This lifting can help also with rescue breaths, as a ventilator may become less necessary.

Figure 21:
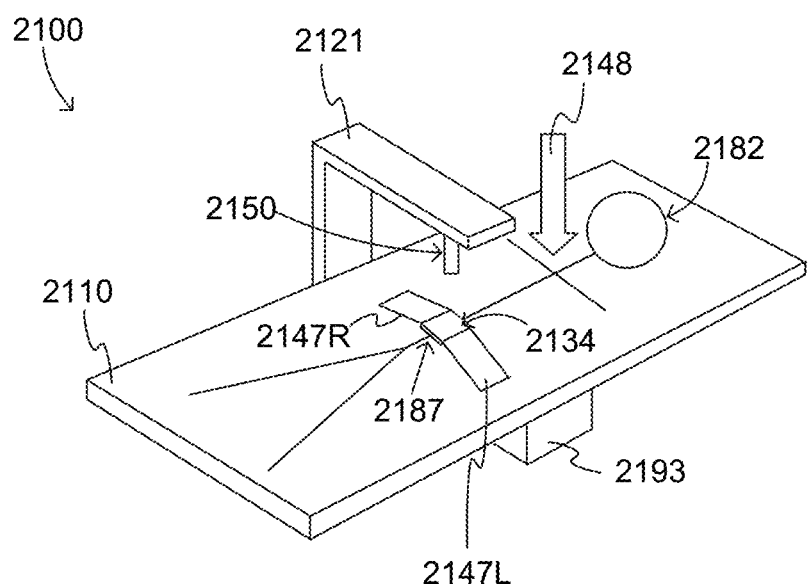
FIG. 21 is a perspective diagram of the CPR system of FIG. 18, made according to a sample embodiment where the auxiliary compression mechanism includes a belt and a piston compressing over the belt.

FIG. 21 is a perspective diagram of a CPR system 2100. CPR system 2100 includes a back plate or platform 2110 that is configured to receive a patient 2182 supine. A main compression mechanism 2148 is configured to perform main chest compressions, similarly with FIG. 18.

An auxiliary compression mechanism 2150 is configured to perform auxiliary chest compressions at a second location 2187 on an abdomen of patient 2182. In FIG. 21, a belt made from a right belt 2147R and a left belt 2147L is buckled by a buckle 2134, and operates as a load-distributing band. A motor 2193 may retract and release the belt. In addition, the retention structure further includes an arm 2121 configured to become coupled to back plate 2110. Auxiliary compression mechanism 2150 includes a piston that is coupled to arm 2121. The piston compresses patient 2182 by compressing the belt. More pistons could be included to compress patient 2182 over the belt.

This arrangement could be provided also for the compressions to the chest, or only for the compressions to the chest. In some of these embodiments, the belt is merely applied with some pressure, but not retracted and released. And, in some of these embodiments, one of the belt and the piston can be considered to be the main compression mechanism, and the other can be considered to be the auxiliary mechanism.

In other words, other versions of CPR systems that are usable by a rescuer to care for a patient may include a back plate configured to receive supine a body of the patient, a belt configured to be placed over the supine body, the belt having ends attached to the back plate, a main motor coupled to the back plate, and a first piston coupled to the back plate and configured to be driven by the main motor so as to perform first or main compressions alternating with releases to the body through the belt.

In such versions, the first compressions can be performed on a chest of the body or an abdomen of the body. Moreover, such versions can also include an auxiliary motor coupled to the back plate and configured to retract and release the belt. Or, they can also include an arm configured to become coupled to the back plate, and in which the first piston is coupled to the arm. Or, they can also include a second piston coupled to the back plate and configured to perform second compressions alternating with releases to the body through the belt. In the latter case, an arm could be further included that is configured to become coupled to the back plate, and in which the first piston and the second piston are coupled to the arm. The pistons could also have suction cups to lift against the belt, if elastic enough, and so on. In another embodiment, the timing or velocity of each piston in an array of pistons could be varied to provide variable patterns in active decompression of the surface of the chest.

Returning to FIG. 17, regardless of where exactly on the patient's body they are performed, the main compressions and the auxiliary compressions can be coordinated for synergistic effects. Examples are now described.

Figure 22:
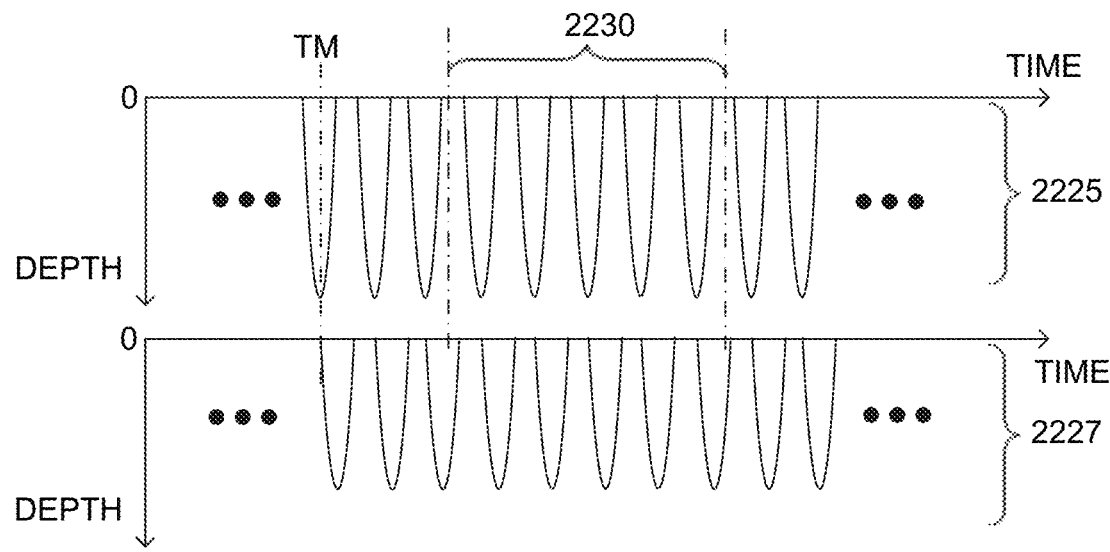
FIG. 22 shows two time diagrams of sample main compressions and auxiliary compressions that are coordinated according to embodiments.

FIG. 22 shows a time diagram of main compressions 2225, and a time diagram of auxiliary compressions 2227. In some versions at least some of auxiliary compressions 2227 are performed with the same frequency as respective ones of main compressions 2225. Indeed, in FIG. 22 there is 1:1 correspondence of the compressions. The numbers of these compressions can be counted within, say, a time interval 2230, for determining frequency, etc.

In FIG. 22, at least some of auxiliary compressions 2227 can be performed in coordination with respective ones of main compressions 2225. Indeed, as will be observed at a time TM, auxiliary compressions 2227 start when main compressions 2225 reach their peak. Accordingly, auxiliary compressions 2227 lag and are not in phase with main compressions 2225. This can help in situations where blood is driven from one place, then to another.

Figure 23:
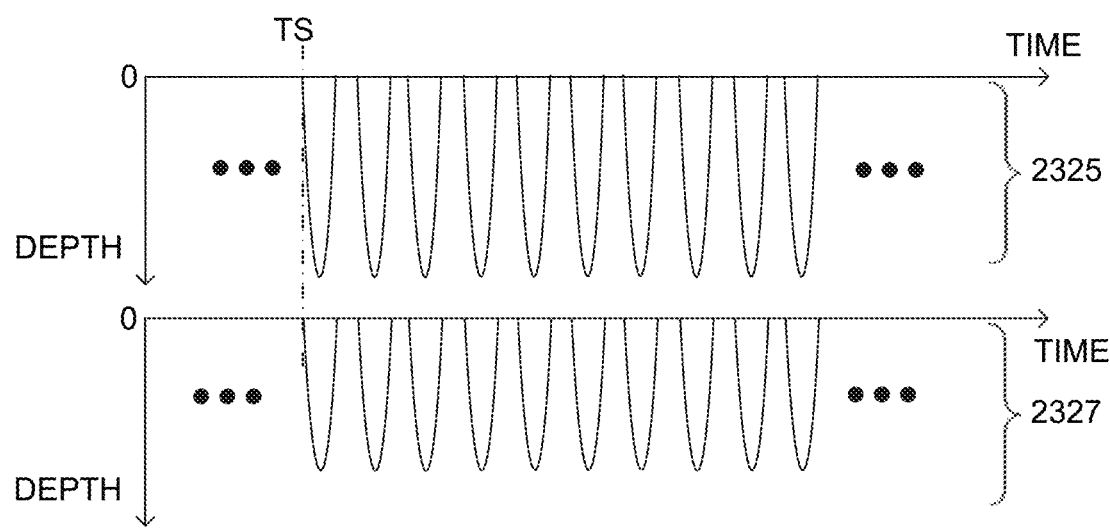
FIG. 23 shows two time diagrams of sample main compressions and auxiliary compressions that are performed simultaneously according to embodiments.

FIG. 23 shows a time diagram of main compressions 2325, and a time diagram of auxiliary compressions 2327. As can be seen starting from time TS, at least some of auxiliary compressions 2327 are performed concurrently with respective ones of main compressions 2325. This happens because these pulses also have the same duration. Since they start at the same times, they are also in phase.

Returning to FIG. 17, in some versions, CPR system 1700 further includes a sensor 1746. Sensor 1746 can be configured to sense a parameter of patient 1782. In such embodiments, at least some of the main compressions and the auxiliary compressions are performed at times determined from the sensed parameter of the patient.

Sensor 1746 can be implemented in a number of ways, some of which were described earlier in this document for consciousness detector 446. For example, sensor 1746 can include a motion detector that is configured to detect a motion of patient 1782. For another example, sensor 1746 can include an electrode that is configured to sense an electrical signal of the patient. For one more example, sensor 1746 may include a camera, configured to acquire an image of the patient, for example as described above. Two more examples are now described.

FIG. 24 is a diagram of a sensor 2446 being implemented by a ventilator. Indeed, sensor 2446 includes a ventilator configured to be placed over a mouth 2483 of patient 2482, and to detect an aspect of a breath of patient 2482. In FIG. 24 the patient's eyes 2484 are shown as shut, and that is how they might be registered by a consciousness detector.

Figure 25:
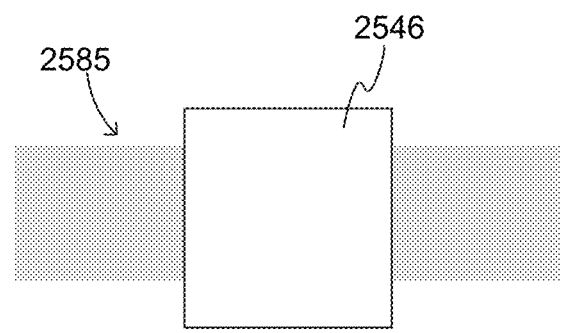
FIG. 25 is a diagram of a sample sensor being implemented by an NIBP cuff according to embodiments.

FIG. 25 is a diagram of a sensor 2546 being implemented by a Non-Invasive Blood Pressure (NIBP) cuff. Indeed, sensor 2546 includes an NIBP cuff configured to be placed around an extremity 2585 of the patient, and to detect a change in the blood pressure of the patient. Extremity 2585 could be an arm, a leg, etc.

Returning to FIG. 17, in some versions, CPR system 1700 further includes a processor (P) 1742. Processor 1742 can be coupled to retention structure 1740, for example as described for processor 442. A memory (M) 1741 can be provided for processor 1742 with instructions that can be read, etc.

Processor 1742 can be configured to control an operation of main compression mechanism 1748 or auxiliary compression mechanism 1747, or both. This controlling may be performed by controlling main motor 1743 and/or auxiliary motor 1749. And this controlling may be performed so that the timing of the main compressions and the auxiliary compressions is and remains coordinated. In some versions, both main compression mechanism 1748 and auxiliary compression mechanism 1747 are thus controlled, so they are coordinated from the beginning.

In other versions, processor 1742 controls one of the compressions mechanisms so as to match the compressions by the other, which could be happening independently. For one example, in some versions, processor 1742 is configured to control an operation of auxiliary compression mechanism 1747 such that a timing of at least one of the auxiliary compressions is coordinated with the performing of at least one of the main compressions or releases from the main compressions, which could be happening independently.

For another example, in some versions, processor 1742 is configured to control an operation of main compression mechanism 1748 such that a timing of at least one of the main compressions is coordinated with the performing of at least one of the auxiliary compressions or releases from the auxiliary compressions, which could be happening independently.

In some versions, sensor 1746 is configured to sense a parameter of patient 1782. In such versions, processor 1742 can be configured to control the operation of main compression mechanism 1748 or auxiliary compression mechanism 1747 according to the sensed parameter.

In some versions, the parameter of patient 1782 that is sensed by sensor 1746 is a sensed timing of the patient's body receiving a compression. For example, the sensed patient parameter can be a sensed timing of the patient's body receiving a certain one of the main compressions. In such versions, processor 1742 can be configured to control an operation of auxiliary compression mechanism 1747 such that a timing of at least one of the auxiliary compressions is coordinated with respect to the timing of the certain main compression. For another example, the sensed patient parameter can be a sensed timing of the patient's body receiving a certain one of the auxiliary compressions. In such versions, processor 1742 can be configured to control an operation of main compression mechanism 1748 such that a timing of at least one of the main compressions is coordinated with respect to the sensed timing of the certain auxiliary compression.

Returning to FIG. 17, embodiments may also benefit from what was described earlier in this document. For example, the processor may permit operation in the tranquil mode, and so on.

In yet other embodiments, a single CPR system does not have dual compression mechanisms in its own right. Rather, it can have a single main compression mechanism, for example for the chest, and be extensible so that it may interoperate with auxiliary devices that provide auxiliary compressions. Such interoperation may be by communicating with such other devices, in a wired way with ports or a wireless way with communications modules. In addition, such interoperation may enable the main compressions of the CPR system to become coordinated with the auxiliary compressions by enabling cooperation in a master-slave configuration, with either device being able to be the master or the slave, protocols to resolve collisions of contradictory commands, and so on. In such versions, a single one of the interoperating devices may project in its user interface status and other information from the other, present options about the other, etc.

In yet other embodiments, a single CPR system does not necessarily have dual compression mechanisms in its own right, nor does it communicate expressly with other devices. Rather, it has ways of sensing whether auxiliary compressions are being performed by another device, when operating in a sense mode. The sense mode can be augmented by a follower mode, where the main compressions are then delivered in coordination with the sensed auxiliary compressions.

Figure 26:
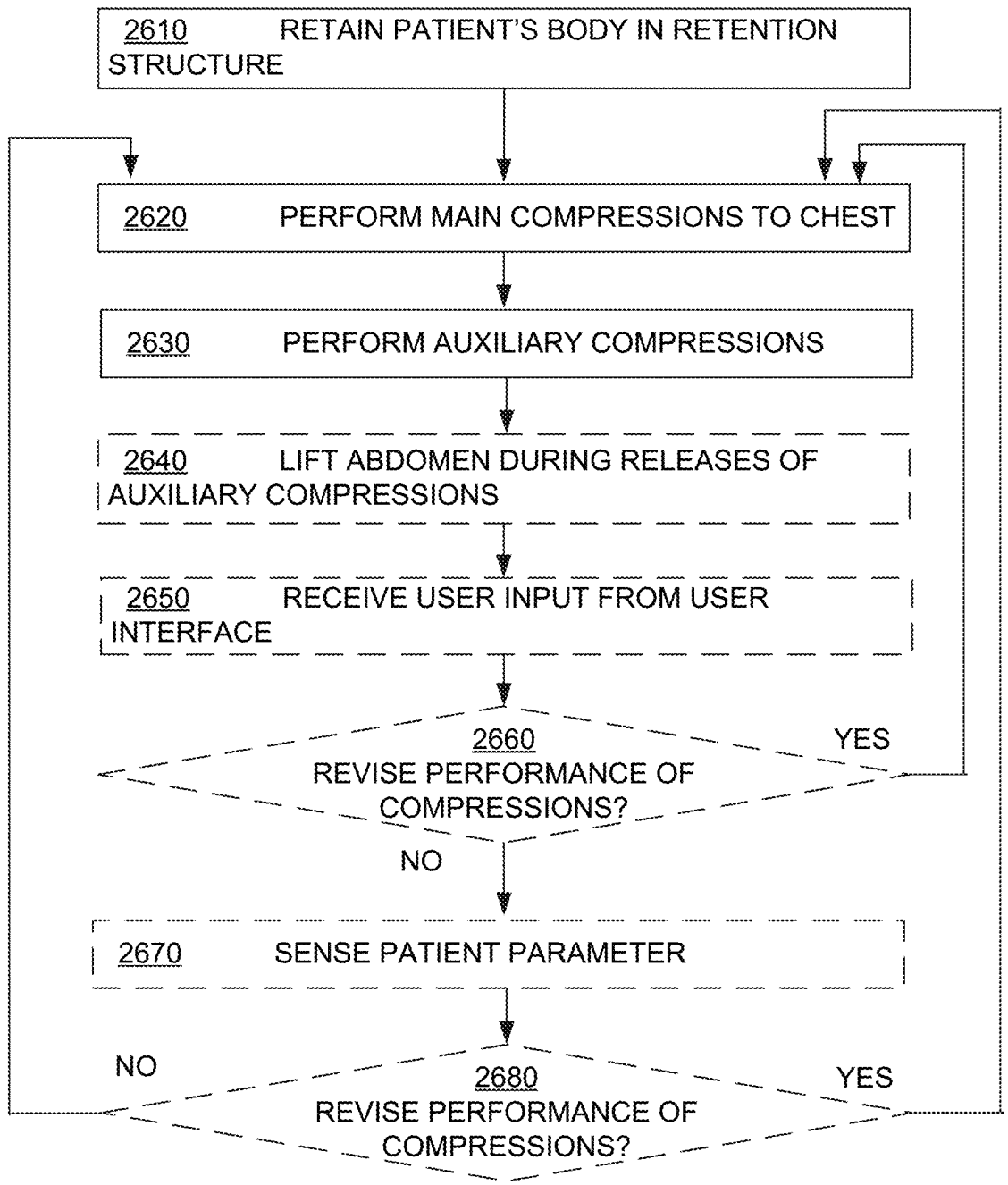
FIG. 26 is a flowchart for illustrating methods according to embodiments.

FIG. 26 shows a flowchart 2600 for describing methods according to embodiments. According to an operation 2610, a patient's body is retained in a retention structure.

According to another operation 2620, main compressions alternating with releases may be performed automatically to a chest of the body by a main compression mechanism and while the body is retained by the retention structure. These main compressions can be CPR compressions, such that they cause the chest to become compressed by at least 2 cm. The releases from the main compressions may be called main releases.

According to another operation 2630, auxiliary compressions alternating with releases may be performed automatically to the body by an auxiliary compression mechanism and while the body is retained by the retention structure. Operation 2630 may take place concurrently with operation 2620. The releases from the auxiliary compressions may be called auxiliary releases. Operation 2630 may be performed to the chest, to the abdomen, an extremity, etc.

If operation 2630 is performed to the abdomen then, according to another, optional operation 2640, the abdomen may be lifted during the auxiliary releases. Such lifting may be above the normal at the time resting vertical level of the abdomen.

According to another, optional operation 2650, a user input may be received from a user interface. According to another, optional operation 2660, it is inquired whether the performance of the compressions needs to be revised in view of operation 2650. If yes, execution may return to operation 2620, or perhaps to 2630, with the compression parameters revised.

If not, then according to another, optional operation 2670, a patient parameter may be sensed. According to another, optional operation 2680, it is inquired whether the performance of the compressions needs to be revised in view of operation 2650. If yes, execution may return to operation 2620, or perhaps to 2630, with the compression parameters revised. If not, execution may return to operation 2620 with the compression parameters not revised.

Due to either operation 2660 or 2680, the compression parameters may be revised. Such a parameter can be the timing, the frequency (also known as rate and repetition rate), another the duty ratio, and so on. In some versions, an operation of the auxiliary compression mechanism is controlled such that a timing of at least one of the auxiliary compressions becomes coordinated with the performing of at least one of the main compressions or releases from the main compressions. In some versions, an operation of the main compression mechanism is controlled such that a timing of at least one of the main compressions becomes coordinated with the performing of at least one of the auxiliary compressions or releases from the auxiliary compressions.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

This disclosure, which may be referenced elsewhere as 3198, is meant to be illustrative and not limiting on the scope of the following claims.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A Cardio-Pulmonary Resuscitation (CPR) system that is usable by a rescuer to care for a patient, the CPR system comprising:
    a retention structure configured to retain a body of the patient;
    a compression mechanism attached to the retention structure and configured to perform automatic CPR compressions alternating with releases to a chest of the body while the body is retained; and
    a processor coupled to the retention structure and configured to:
        control the compression mechanism to compress the chest by at least 2 centimeters in a tranquil mode and a normal mode, the tranquil mode including at least a first chest compression time interval of 15 seconds when chest compressions are performed at an average chest compression frequency between 0.5 compressions per minute (cpm) and 52 cpm, and the normal mode including a second chest compression time interval of greater than 15 seconds when chest compressions are performed at an average chest compression frequency equal to or greater than 64 cpm, and
        automatically revert to operating in the normal mode after operating in the tranquil mode for a threshold time duration.

2. The CPR system of claim 1, in which
during the first time interval the average frequency is between 0.5 cpm and 48 cpm.

3. The CPR system of claim 1, in which
during the first time interval the average frequency is between 0.5 cpm and 44 cpm.

4. The CPR system of claim 1, in which
during the first time interval all the chest compressions are performed at a single frequency.

5. The CPR system of claim 1, in which
during the first time interval of the tranquil mode the chest compressions are performed in two groups at a single frequency, while no compressions are performed during a set pause of at least 3 sec between the two groups.

6. The CPR system of claim 1, in which
during the first time interval of the tranquil mode at least some of the chest compressions are performed at a plurality of instantaneous frequencies.

7. The CPR system of claim 1, in which the processor is further configured to:
    control the compression mechanism during the tranquil mode to compress the chest during a third time interval that immediately follows the first time interval, lasts at least 30 sec, and is distinct from the second interval, the chest compressions are performed at an average frequency between 0.5 cpm and 56 cpm.

8. The CPR system of claim 7, in which
during the third time interval the average frequency is between 0.5 cpm and 48 cpm.

9. The CPR system of claim 7, in which
during the third time interval the average frequency is between 0.5 cpm and 44 cpm.

10. The CPR system of claim 7, in which
during the third time interval all the chest compressions are performed at a single frequency.

11. The CPR system of claim 7, in which
during the third time interval the chest compressions are performed in two groups at a single frequency, while no compressions are performed during a set pause of at least 3 sec between the two groups.

12. The CPR system of claim 7, in which
during the third time interval at least some of the chest compressions are performed at a plurality of instantaneous frequencies.

13. The CPR system of claim 1, further comprising:
a consciousness detector configured to be operatively coupled to the processor, the consciousness detector further configured, after at least 20 chest compressions have been performed, to detect a patient parameter and to output a series of consciousness values determined from the detected patient parameter, and in which the processor is further configured to receive an early and a later distinct consciousness values of the series and, if the later consciousness value is different from the early consciousness value, control the compression mechanism to change a current average frequency of performing the chest compressions from a first value to a second value, the current average frequency measured over a 15 sec time interval.

14. The CPR system of claim 13, in which performing the chest compressions is paused for a pause interval occurring after the later consciousness value is received and before the chest compressions start being performed at a current average frequency having the second value.

15. The CPR system of claim 13, in which the consciousness detector includes a motion detector configured to detect a motion of the patient.

16. The CPR system of claim 13, in which the consciousness detector includes an electrode configured to capture an electrical signal of the patient.

17. The CPR system of claim 13, in which the consciousness detector includes a camera configured to capture an image of the patient.

18. The CPR system of claim 1, further comprising:

a consciousness detector operatively coupled to the processor and configured to detect a patient parameter and to output test consciousness values that are determined from the detected patient parameter and are associated with performed test compressions, and in which the processor is further configured to:

control the compression mechanism to perform test chest compressions having time spacings between successive ones of the test compressions have with at least two different values, determine an optimal frequency from at least some of the test consciousness values, and during an optimization mode, control the compression mechanism to perform the chest compressions at the optimal frequency plus or minus 20% for at least 15 seconds.

19. The CPR system of claim 18, in which the time spacings increase with time.

20. The CPR system of claim 18, in which the time spacings decrease with time.

21. The CPR system of claim 18, in which during the optimization mode, the processor is further configured to control the compression mechanism to perform the chest compressions at the optimal frequency plus or minus 20% for at least 30 seconds.

22. The CPR system of claim 18, in which during the optimization mode, the processor is further configured to control the compression mechanism to perform the chest compressions at the optimal frequency for at least 15 seconds.

23. The CPR system of claim 1, further comprising:

a user interface operatively coupled with the processor and configured to receive a control input from a human and to change, responsive to the received control input, from operating in one of the tranquil mode and the normal mode to operating in the other one of the tranquil mode and the normal mode.

24. The CPR system of claim 23, further comprising:

a voice recognition module; and in which the user interface includes a microphone configured to capture a sound as the control input, the voice recognition module is configured to recognize whether or not the captured sound resulted from a preset utterance, and if the voice recognition module recognized the captured sound as having resulted from the preset utterance, the processor is further configured to change from operating in one of the tranquil mode and the normal mode to operating in the other one of the tranquil mode and the normal mode.

25. The CPR system of claim 24, in which the user interface further includes a speaker configured to speak an instruction to the patient to vocalize the preset utterance if the patient is unbearably uncomfortable.

26. The CPR system of claim 1, further comprising:

an auxiliary compression mechanism distinct from the compression mechanism, the auxiliary compression mechanism coupled to the retention structure and configured to perform, while the body is thus retained, automatically auxiliary compressions alternating with releases to the body.

27. A Cardio-Pulmonary Resuscitation (CPR) system that is usable by a rescuer to care for a patient, the CPR system comprising:

a retention structure configured to retain a body of the patient;

a compression mechanism attached to the retention structure and configured to perform, while the body is thus retained, automatic CPR compressions alternating with releases to a chest of the body;

a processor coupled to the retention structure and configured to:

control the compression mechanism to compress the chest by at least 2 cm in a tranquil mode and a normal mode, the tranquil mode including at least a first chest compression time interval equal to or greater than 10 seconds when chest compressions are performed at a first average frequency between 0.5 compressions per minute (cpm) and 52 cpm and the normal mode including a second chest compression time interval equal to or greater than 10 seconds when chest compressions are performed at a second average frequency higher than the first average frequency responsive to the chest compressions having been performed at the first average frequency for a threshold time duration, and automatically revert to operating in the normal mode after operating in the tranquil mode for a threshold time duration.

28. The CPR system of claim 27, in which the first average frequency is less than 90 cpm.

29. The CPR system of claim 27, in which the second average frequency is greater than 90 cpm.

30. The CPR system of claim 27, in which the threshold time duration is at least 45 sec.

31. The CPR system of claim 27, in which the threshold time duration is at least 180 sec.

* * * * *